United States Patent
McCarthy et al.

(10) Patent No.: US 12,128,270 B2
(45) Date of Patent: Oct. 29, 2024

(54) SYSTEMS AND METHODS FOR NEUROLOGIC REHABILITATION

(71) Applicant: MedRhythms, Inc., Portland, ME (US)

(72) Inventors: Owen McCarthy, Gorham, ME (US); Brian Harris, Gray, ME (US); Alex Kalpaxis, Glendale, NY (US); Eric Richardson, Portland, ME (US); Ryan Foley, Portland, ME (US)

(73) Assignee: MedRhythms, Inc., Portland, ME (US)

( * ) Notice: Subject to any disclaimer, the term of this patent is extended or adjusted under 35 U.S.C. 154(b) by 868 days.

(21) Appl. No.: 17/096,321

(22) Filed: Nov. 12, 2020

(65) Prior Publication Data

US 2021/0086024 A1 Mar. 25, 2021

Related U.S. Application Data

(63) Continuation-in-part of application No. 16/569,388, filed on Sep. 12, 2019, now Pat. No. 11,779,274,
(Continued)

(51) Int. Cl.
*A63B 22/00* (2006.01)
*A61B 5/11* (2006.01)
*G16H 20/30* (2018.01)

(52) U.S. Cl.
CPC .............. *A63B 22/00* (2013.01); *A61B 5/112* (2013.01); *G16H 20/30* (2018.01);
(Continued)

(58) Field of Classification Search
CPC ............ A63B 22/00; A63B 2022/0092; A63B 2022/0094; A63B 2220/10;
(Continued)

(56) References Cited

U.S. PATENT DOCUMENTS

| 8,212,136 B2 * | 7/2012 | Shirai ................ A63B 71/0686 84/610 |
| 2010/0075806 A1 * | 3/2010 | Montgomery ....... G09B 19/003 600/23 |

(Continued)

OTHER PUBLICATIONS

Thaut et al. "Rhythmic Auditory Stimulation in Rehabilitation of Movement Disorders: A Review of Current Research", Rhythmic Auditory Stimulation in Rehabilitation, Oct. 12, 2009. Retrieved on May 1, 2021. Retrieved from <URL:https://pdfs.semanticscholar.org/91ea/4f13f25f0ce0d68422a403ba26742a35d47e.pdf> entire document.

(Continued)

*Primary Examiner* — Benjamin S Melhus
(74) *Attorney, Agent, or Firm* — Leason Ellis LLP

(57) ABSTRACT

A method and system for rehabilitation of a patient having a physical impairment by providing repetitive motion therapy is disclosed. The system is configured to receive biomechanical data from the patient regarding repetitive movements of the patient performed using a first and second side of the body, respectively, and select, based on the data, an entrainment side according to which repetitive motion therapy is provided. The system further performs repetitive motion therapy by: providing the patient auditory stimulus comprising beat signals output at respective beat times; receiving time-stamped biomechanical data for repetitive movements performed by the patient using the entrainment side in relation to the respective beat times of the beat signals; calculating an entrainment potential for the entrainment side by comparing a timing of the repetitive movements to the timing of the beat signals; and modifying the auditory stimulus as a function of the calculated entrainment potential.

18 Claims, 32 Drawing Sheets

Related U.S. Application Data which is a continuation of application No. 15/488,201, filed on Apr. 14, 2017, now Pat. No. 10,448,888.

(60) Provisional application No. 62/934,457, filed on Nov. 12, 2019, provisional application No. 62/322,504, filed on Apr. 14, 2016.

(52) U.S. Cl.
CPC ........ *A63B 2022/0092* (2013.01); *A63B 2022/0094* (2013.01); *A63B 2220/10* (2013.01); *A63B 2220/803* (2013.01); *A63B 2230/08* (2013.01)

(58) Field of Classification Search
CPC .......... A63B 2220/803; A63B 2230/08; A61B 5/112; A61B 5/7264; A61B 2562/0219; A61B 5/4836; A61B 5/1128; A61B 5/389; A61B 5/7275; A61B 5/1124; A61B 5/486; A61B 5/002; A61B 5/0077; G16H 20/30; G16H 20/90; G16H 40/63; G16H 50/30

See application file for complete search history.

(56) References Cited

U.S. PATENT DOCUMENTS

| | | |
|---|---|---|
| 2011/0166488 A1* | 7/2011 | Miyake ............... A61H 3/00 601/34 |
| 2014/0307878 A1 | 10/2014 | Osborne et al. |
| 2017/0296116 A1 | 10/2017 | McCarthy et al. |
| 2019/0022351 A1 | 1/2019 | McCarthy et al. |
| 2020/0214615 A1 | 7/2020 | Bass |

OTHER PUBLICATIONS

Woerd et al. "Impaired auditory-to-motor entrainment in Parkinson's disease", J Neurophysiol 117: 1853-1864, Aug. 2, 2017. Retrieved on: May 1, 2021. Retrieved from <URL:https://journals.physiology.org/doipdf/10.1152jn.00547.2016> entire document.

International Search Report and Written Opinion dated Feb. 4, 2021 corresponding to International Patent Application No. PCT/US2020/060220; 8 pages.

* cited by examiner

SYSTEMS AND METHODS FOR NEUROLOGIC REHABILITATION

CROSS-REFERENCE TO RELATED APPLICATIONS

This application is a continuation-in-part of U.S. patent application Ser. No. 16/569,388 filed on Sep. 12, 2019, entitled "Systems and Methods for Neurologic Rehabilitation," and is further based on and claims benefit of U.S. Provisional Patent Application No. 62/934,457 filed on Nov. 12, 2019, entitled "Systems and Methods for Neurologic Rehabilitation," which are each hereby incorporated by reference in their respective entireties herein.

TECHNICAL FIELD

The present disclosure relates generally to systems and methods for rehabilitation of a user having a physical impairment by providing music therapy.

BACKGROUND

Many controlled studies over the past decade have emphasized the clinical role of music in neurologic rehabilitation. For example, regimented music therapy is known to directly enable cognition, motor and language enhancement. The process of listening to music enhances brain activity in many forms, igniting a widespread bilateral network of brain regions related to attention, semantic processing, memory, cognition, motor function and emotional processing.

Clinical data supports music therapy enhancing memory, attention, executive function, and mood. PET scan research on the neural mechanisms behind music revealed that pleasant music can stimulate a widespread network between the cortical and subcortical region including the ventral striatum, nucleus accumbens, amygdala, insula, hippocampus, hypothalamus, ventral tegmental area, anterior cingulate, orbitofrontal cortex, and ventral medial prefrontal cortex. The ventral tegmental area produces dopamine and has a direct connection to the amygdala, hippocampus, anterior cingulate and prefrontal cortex. This mesocorticolimbic system, which can be activated by music, plays a critical role in mediating arousal, emotion, reward, memory attention, and executive function.

Neuroscience research has revealed how the fundamental organization processes for memory formation in music shares a mechanism with the non-musical memory processes. The basis of phrase groupings, hierarchical abstractions, and musical patterns have direct parallels in temporal chunking principles for non-musical memory processes. This implies that memory processes activated with music could translate and enhance non-musical processes.

Accordingly, there remains a need for improved devices, systems, and methods for protecting the use of user identity and for securely providing personal information.

SUMMARY

In one aspect of the disclosed subject matter, a method is provided for rehabilitation of a patient having a physical impairment by providing repetitive motion therapy in which the patient is provided auditory stimulus having beat signals and the patient attempts to perform repetitive movements using a first side and an opposite second side of the patient's body in time with the beat signals. The method is implemented on a computer system having a processor configured by machine-readable instructions which, when executed perform the method.

In particular, the method comprises the step of receiving, at the computer system, biomechanical data for the patient regarding repetitive movements of the patient performed using the first and second sides of the body respectively. The method also includes selecting, by the computer system based on the received biomechanical data, an entrainment side, wherein the entrainment side is one of the first or the second side of the body.

Additionally, the method includes performing, by the computer system, repetitive motion therapy. The step of performing repetitive motion therapy includes outputting, to the patient, auditory stimulus comprising beat signals output at respective beat times and receiving time-stamped biomechanical data of the patient relating to the repetitive movements performed by the patient using at least the entrainment side in relation to the beat signals. The step of performing repetitive motion therapy further includes calculating an entrainment potential for the entrainment side, wherein the entrainment potential is calculated by comparing a timing of the repetitive movements performed by the patient using the entrainment side to the respective beat times of the beat signals. Additionally, performing repetitive motion therapy includes modifying the auditory stimulus as a function of the calculated entrainment potential.

According to a further aspect, a system is provided for rehabilitation of a patient having a physical impairment by providing repetitive motion therapy in which the patient is provided auditory stimulus having beat signals and the patient attempts to perform repetitive movements using a first side and an opposite second side of the patient's body in time with the beat signals. The system comprises a computer system having a processor configured by machine-readable instructions to receive biomechanical data for the patient regarding repetitive movements of the patient performed using the first and second sides of the body respectively, wherein the biomechanical data is measured using a sensor associated with the patient. Additionally the processor is configured to select, based on the received biomechanical data, an entrainment side, wherein the entrainment side is one of the first or the second side of the body.

Furthermore, the processor is configured to perform repetitive motion therapy by outputting to the patient auditory stimulus comprising beat signals output at a respective beat times and receiving time-stamped biomechanical data of the patient relating to the repetitive movements performed by the patient using at least the entrainment side in relation to the beat signals. The biomechanical data is measured using a sensor associated with the patient. Additionally, the processor is configured to perform repetitive motion therapy by calculating an entrainment potential for the entrainment side and by modifying the auditory stimulus as a function of the calculated entrainment potential. In particular, the entrainment potential is calculated by comparing a timing of the repetitive movements performed by the patient using the entrainment side to the respective beat times of the beat signals.

BRIEF DESCRIPTION OF THE DRAWINGS

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein.

DETAILED DESCRIPTION

The present invention relates generally to systems, methods and apparatus for implementing a dynamic closed-loop rehabilitation platform system that monitors and directs human behavior and functional changes. Such changes are in language, movement, and cognition that are temporally triggered by musical rhythm, harmony, melody, and force cues.

Figure 1:
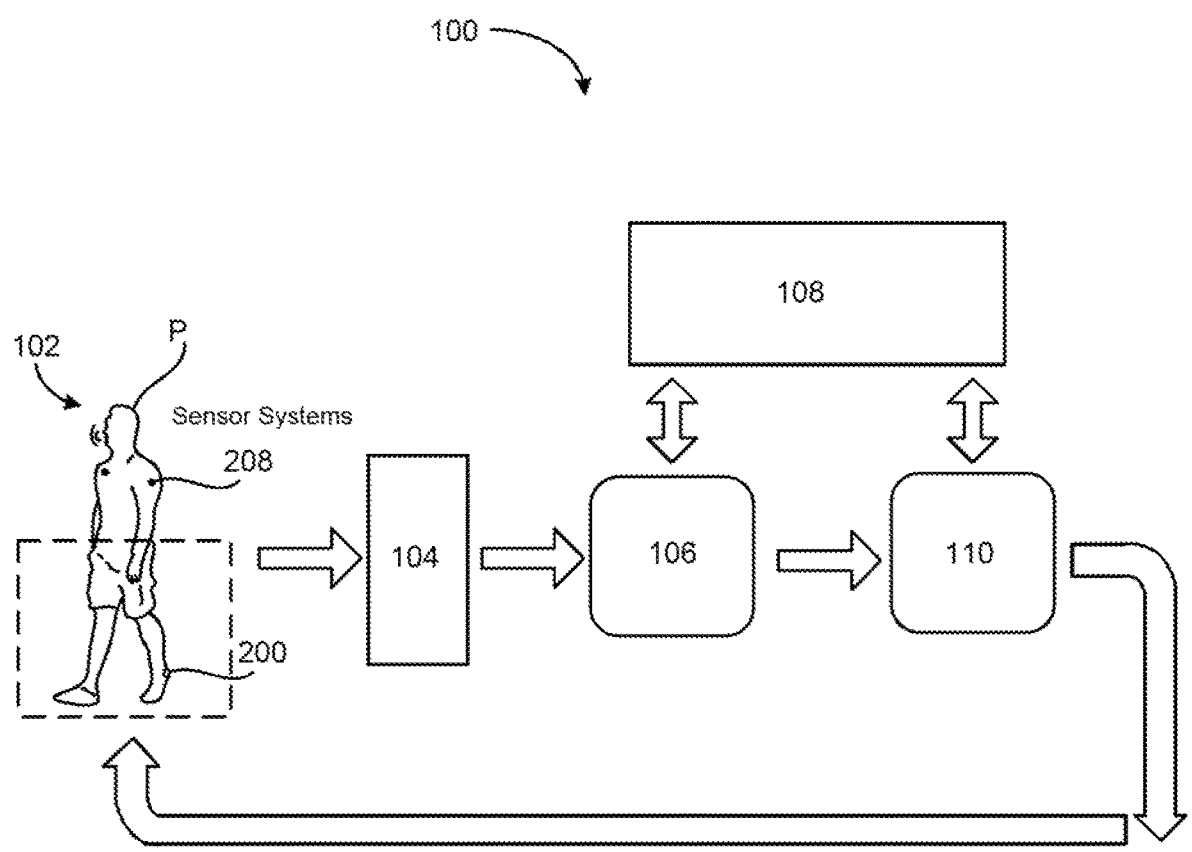
FIG. 1 is a diagram illustrating a system for therapy of a user by providing music therapy in accordance with exemplary embodiments of the disclosed subject matter.

In various embodiments of the invention, a dynamic closed-loop rehabilitation platform music therapy system 100 is provided illustrated in FIG. 1, which includes sensor components and systems 102, edge-processing components 104, collector components 106, analytics systems 108, and music therapy center 110. As will described in greater detail below, the sensor components, edge processing components, collector components machine learning processes and music therapy center may be provided on various hardware components. For example, in one embodiment, the sensor components and edge processing components may be located or worn by the patient. In such embodiments, the collector components and music therapy center may be provided on a handheld device. In such embodiments the analytics systems may be located on a remote server.

Sensor Systems

Throughout the description herein, the term "patient" is used to refer to the individual receiving musical therapy treatment. The term "therapist" is used to refer to the individual providing musical therapy treatment. In some embodiments, the patient is able to interact with this system described herein without the presence of the therapist to administer the treatment.

The sensor components 102 provide sensed biomechanical data about the patient. In some embodiments, the sensor components can include (1) wearable wireless real-time motion sensing devices or IMU (inertial measurement units), (2) wearable wireless real-time combination multiple zone foot plantar pressure/6-dimensional motion capture (IMU) devices, such as sensor 200, (3) wearable wireless real-time Electromyogram (EMG) devices, such as sensor 208, (4) real-time wireless near infrared (NIR) video capture devices, such as imaging device 206 (See FIG. 4)

Figure 2:
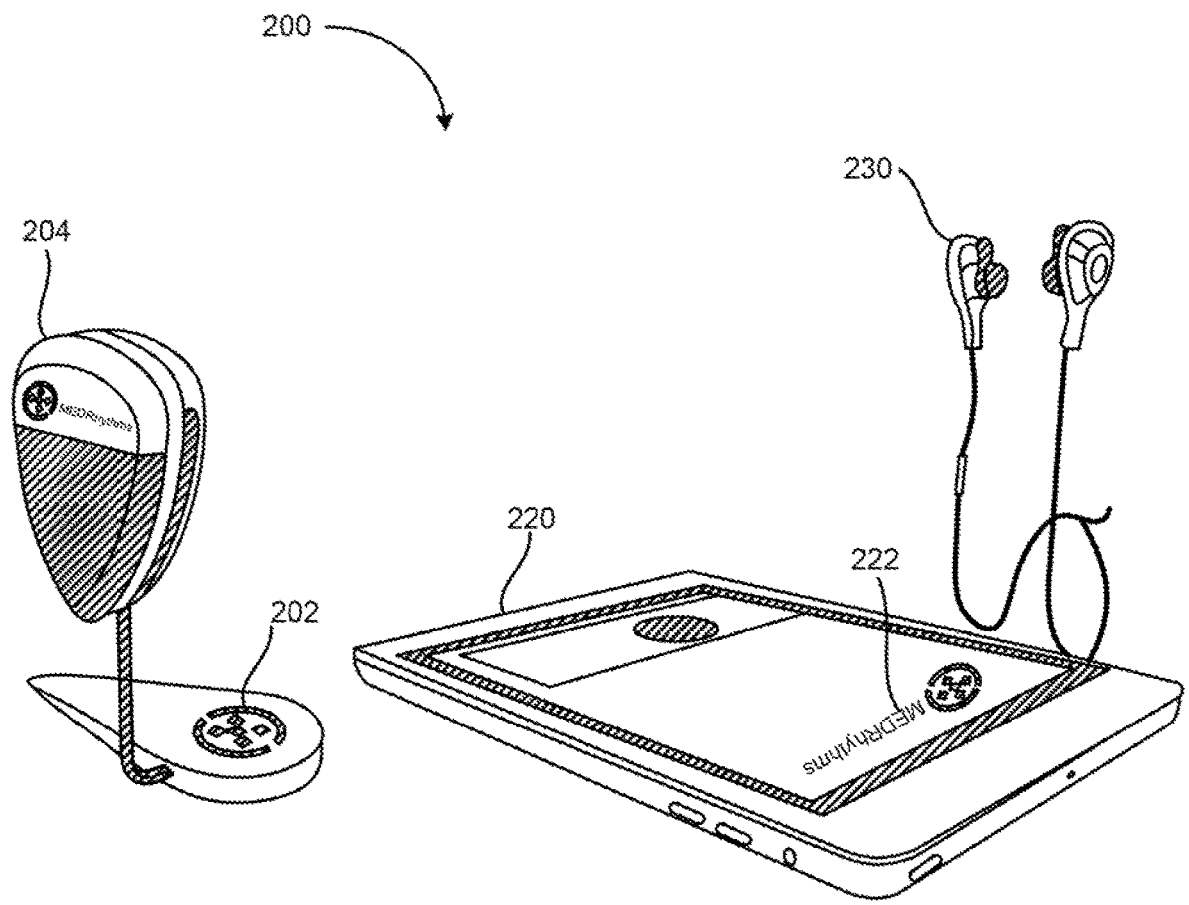
FIG. 2 is a diagram illustrating several components of a system for rehabilitation of a user by providing music therapy in accordance with exemplary embodiments of the disclosed subject matter.

As illustrated in FIG. 2, the systems and methods described herein are used in connection with treating walking disorders of the patient. Accordingly, the exemplary sensor 200 can be a combination multiple zone foot plantar pressure/6-degrees of freedom motion capture device. Sensor 200 records the patient's foot pressure and 6-degrees of freedom motion profile while the patient walks during a music therapy session. In some embodiments, the foot pressure/6-degrees of freedom motion capture device has variable recording duration intervals with a sampling rate of 100 Hz for a foot pressure profile that comprises 1 to 4 zones resulting in 100 to 400 pressure data points per foot per second.

The sensor 200 can include a foot pressure pad 202 having a heel pad (for measuring one zone of pressure, e.g., heel strike pressure) to a full insole pad (for measuring 4 zones of pressure). The pressure measurements are made by sensing the resistive changes in transducer material as a result of the compression due to the patient's weight transferred to the foot. These foot pressure maps are obtained for each sampling interval or at specific instants during a music therapy session.

The sensor 200 can include a 6-Dimensional motion capture device 204 that detects the changes in motion via a 6-degrees of freedom Micro-Electro-Mechanical Systems (MEMS) based sensor which determines linear acceleration in 3 dimensions, $A_x$, $A_y$, $A_z$ and rotational motion as pitch, yaw, and roll. Sampling at 100 Hz will produce 600 motion data points per second. These foot motion captures are obtained for each sampling interval or at specific instants during a music therapy session.

Figure 3:
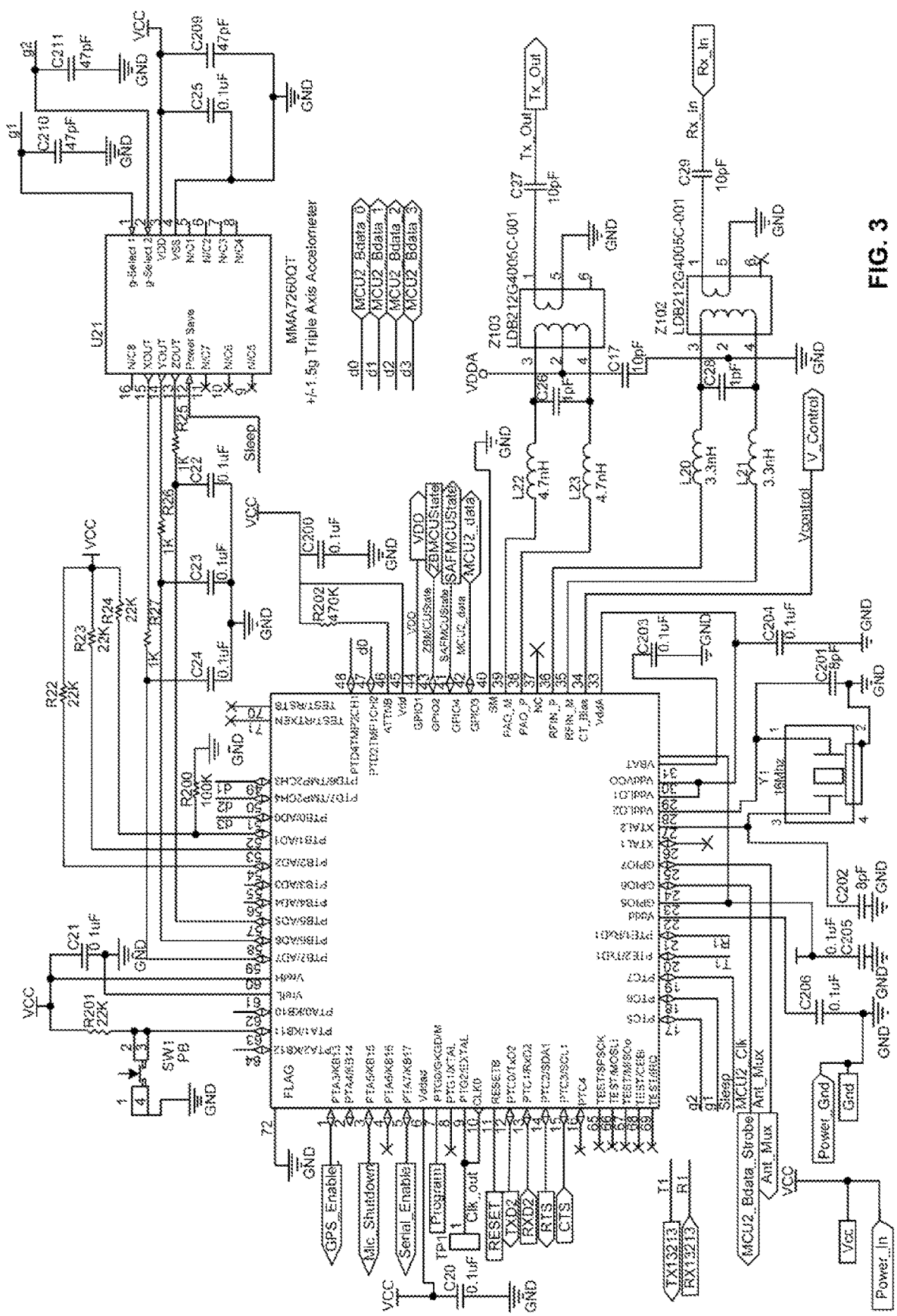
FIG. 3 is a schematic drawing of a sensor for measuring the biomechanical movements of a patient in accordance with exemplary embodiments of the disclosed subject matter.

The multiple zone pressure sensing with the 6-degrees of freedom motion capture device allows for map-able spatial and temporal gait dynamics tracking while walking. A schematic diagram of the sensor 200 is illustrated in FIG. 3.

Figure 4:
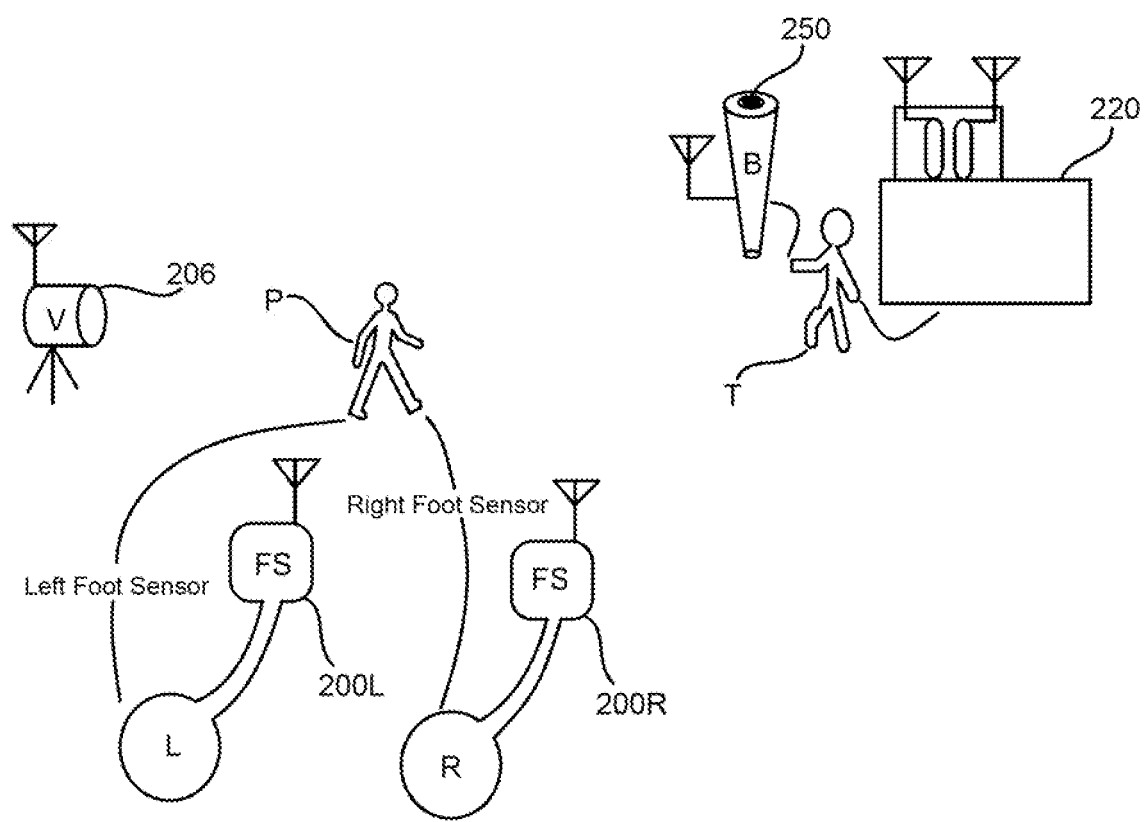
FIG. 4 is a diagram illustrating several components of the system in accordance with exemplary embodiments of the disclosed subject matter.

From a system perspective, as illustrated in FIG. 4, the patient P uses two foot sensors 200, one for each foot designated as Right 200R and Left 200L. In an exemplary embodiment, the right foot sensor 200R wirelessly communicates time-stamped internal measurement unit data and heel strike pressure data over a first channel, e.g., channel 5, in the IEEE 802.15.4 direct sequence spread spectrum (DSSS) RF band. The left foot sensor 200L wirelessly communicates time-stamped internal measurement unit data and heel strike pressure data over a second channel, e.g., channel 6, in the IEEE 802.15.4 direct sequence spread spectrum (DSSS) RF band. A tablet or laptop 220, optionally used by the therapist T, as described below, includes a wireless USB hub containing two IEEE 802.15.4 DSSS RF transceivers tuned to the first and second channels, e.g., channel 5 and 6, in order to capture the right/left foot sensor RF data. A handheld wireless trigger 250 is used to start and stop video and/or to make notations and index the time stream as discussed in greater detail below.

A video analytics domain can be used to extract patient semantic and event information about therapy sessions. Patient actions and interactions are components in the therapy that affect the therapy context and regiment. In some embodiments, one or more image capture devices 206, such as video cameras, (see FIG. 4) are used with a time-synched video feed. Any appropriate video may be incorporated into the system to capture patient movement; however, Near Infrared (NIR) video capture is useful to preserve the patient's privacy and to reduce the video data to be processed. The NIR video capture device captures NIR video images of a patient's body such as the position of the patient's torso and limbs. Further, it captures the patient's real-time dynamic gait characteristics as a function of a music therapy session. In some embodiments, the video is captured with a stationary camera, in which the background is subtracted to segment out foreground pixels.

As illustrated in FIG. 4, the one or more video cameras 206 are triggered by the tablet or laptop application when therapy session starts. The video cameras 206 can be stopped or started by a hand held wireless trigger unit 250 by the therapist. This allows for labeled time-stamped index to be created in the captured biomechanical sensor data and video data streams.

In some embodiments, wearable wireless real-time Electromyogram (EMG) devices 208 can be worn by the patient. EMG sensors provide the entire bi-ped profile for major muscle firing for locomotion. Such sensors provide data regarding the exact time when the muscle are fired.

Edge Processing

In some embodiments, the edge process is performed at the sensors 200, where sensor data is captured from the IMU and pressure sensors. This sensor data is filtered, grouped into various array sizes for further processing into frames reflecting extracted attributes and features, and where these frames are sent, e.g., wirelessly, to the collector 106 on a tablet or laptop. It is understood that the raw biomechanical sensor data obtained from the sensor 200 can alternatively be transferred to a remote processor for the collect for the edge processing functions to take place.

The wearable sensors 200, 208 and the video capture devices 206, generates sensor data streams that are processed holistically to facilitate biomechanical feature extraction and classification. Sensor fusion, combining the outputs from multiple sensors capturing a common event, better captures a result than any single constituent sensor inputs.

Capturing patient activities in the music therapy context formalizes the interactions as applied to the music therapy and in developing patient specific and generalized formal indicators of the music therapy performance and efficacy. Extracting video features and then analyzing allows for the capture of semantic, high-level information about patient behaviors.

In processing video, a learned background subtraction technique is used to create a background model which incorporates any variation in lighting conditions and occlusions in the physical area where music therapy occurs. The result of the background subtraction is a binary foreground map with an array of foreground blobs which are two dimensional contours. Thus, the video is sliced into individual image frames for future image processing and sensor fusion. Video information is provided with additional meta data by merging in the edge-processed sensor data from the IMU, foot pressure pad(s), and EMG sensors. The sensor data can be time synched with the other data using the RF trigger. Data can be sent directly to the collector, stored on the memory of the internal board, or analyzed on the edge running the OpenCV library.

The edge processor 104 can be a microprocessor, such as a 32-bit microprocessor incorporated into the foot pressure/6-degrees of freedom motion capture device that enables fast multiple zone scanning at a rate of 100 to 400 complete foot pressure/6-degrees of freedom motion profiles per second.

The foot pressure/6-degrees of freedom motion capture device collects foot pressure/6-degrees of freedom motion profile data for real-time gait analysis resulting in feature extraction and classification. In some embodiments, the foot pressure/6-degrees of freedom motion capture device initializes an micro controller unit (MCU), continuous operator process (COP), general purpose input output (GPIO), serial peripheral interface (SPI), interrupt request (IRQ), and sets a desired RF transceiver clock frequency by calling routines including micro controller unit initialize (MCUInit), general purpose input output initialize (GPIOInit), serial peripheral interface initialize (SPIInit), interrupt request acknowledge-initialize (IRQInit), interrupt request acknowledge (IRQACK), Serial Peripheral Interface Driver Read (SPI-DrvRead), and IRQPinEnable. MCUInit is the master initialization routine which turns off the MCU watchdog and sets the timer module to use bus clock (BUSCLK) as a reference with a pre-scaling of 32.

The state variable gu8RTxMode is set to SYSTEM_RESET_MODE and the routines GPIOInit, SPIInit and IRQInit are called. The state variable gu8RTxMode is set to RF_TRANSCEIVER_RESET_MODE and the IRQFLAG is checked to see if IRQ is asserted. The RF transceiver interrupts are first cleared using SPIDrvRead, then the RF transceiver is checked for ATTN IRQ interrupts. Lastly, for MCUInit, calls are made to PLMEPhyReset to reset the physical MAC layer, IRQACK (to ACK the pending IRQ interrupt) and IRQPinEnable which is to pin, Enable, IE, and IRQ CLR, on signal's negative edge.

The foot pressure/6-degrees of freedom motion sensor 200 will wait for a response from the foot pressure/6-degrees of freedom motion collecting node, e.g., 250 milliseconds, to determine whether a default full foot pressure scan will be done or a mapped foot pressure scan will be initiated. In the case of a mapped foot pressure scan, the foot pressure/6-degrees of freedom motion collecting node will send the appropriate electrode the foot pressure scan mapping configuration data.

One aspect of the analytics pipeline is the feature set engineering process which will define those captured sensor values and their resulting sensor-fused values that are used to create feature vectors to define the input data structures for the analytics. Representative values are $A_x(i)$, $A_y(i)$, $A_z(i)$, and $Ph(i)$, where i is the ith sample, where $A_x(i)$ is the acceleration in the x-direction which is Lateral in relation to the foot sensor; $A_y(i)$ is the acceleration in the y-direction which is Front in relation to the foot sensor; $A_z(i)$ is the acceleration in the z-direction which is Up in relation to the foot sensor; and $Ph(i)$ is the heel strike pressure. The Sensor values are presented in Table 1:

TABLE 1

Avg (Ax) = Sum [Ax(i) over i = 0 to i = N]/N
Avg (Ax) = Sum [Ax(i) over i = 0 to i = N]/N
Avg (Ay) = Sum [Ay(i) over i = 0 to i = N]/N
Avg (Az) = Sum [Az(i) over i = 0 to i = N]/N
Max (Ax) in the range of Ax(i) from i = 0 to i = N
Max (Ay) in the range of Ay(i) from i = 0 to i = N
Max (Az) in the range of Az(i) from i = 0 to i = N
Min (Ax) in the range of Ax(i) from i = 0 to i = N
Min (Ay) in the range of Ay(i) from i = 0 to i = N
Min (Az) in the range of Az(i) from i = 0 to i = N
Avg (Ph) = Sum [Ph(i) over i = 0 to i = N]/N
Max (Ph) in the range of Ph(i) from i = 0 to i = N
where N = window size In some embodiments, the sensor-fused technique uses the heel strike pressure value Ph(i) to "gate" the analysis of the following exemplary feature values to derive a window of data as will be described below. For example, the "onset" (start) can be determined based on heel pressure exceeding a threshold indicating heel strike, and the "stop" based on heel pressure falling below a threshold indicating heel off, presented in Table 2, below. It is understood, that heel strike pressure is one example of a parameter that can be used to for the "gate" analysis. In some embodiments, "gating" is determined by use of IMU sensor data, video data, and/or EMG data.

TABLE 2

Power Factor PF(i) = Sqrt (Ax(i)2 + Ay(i)2 + Az(i)**2)
Windowed Total Motion Intensity = [Avg(Ax) + Avg(Ay) + Avg(Az)]/3
Windowed Lateral Tremor Intensity = Sum [ (Ax(i) − Ax(i + 1))**2] from i = 0 to i = N
Windowed Total Tremor Intensity =
Sum [(Ax(i) − Ax(i + 1))**2] +
Sum [(Ay(i) − Ay(i + 1))**2] +
Sum [(Az(i) − Az(i + 1))**2] from i = 0 to i = N
Windowed Differential Ax = Max (Ax) − Min (Ax)
Windowed Differential Ay = Max (Ay) − Min (Ay)
Windowed Differential Az = Max (Az) − Min (Az)
where N = window size Higher level feature values are calculated from the fused sensor values, such as exemplary values presented in Table 3:

TABLE 3

Step Count (Total number)
Step Length Right (centimeters - cm)
Step Length Left (cm)
Step Time Right (milliseconds - msec)
Step Time Left (msec)
Asymmetry Factor Right/Left Step Time (Step Time Right - Step Time Left)
Step Width (cm)
Cadence (strides per minute)
Stride Length (cm)
Stride Velocity (cm/sec)
Stride Time Right (msec)
Stride Time Left (msec)
Asymmetry Factor Right/Left Stride Time (Stride Time Right - Stride Time Left)
Stride Tremor (Windowed Lateral Tremor Intensity)
Stride Fluidity (Windowed Total Tremor Intensity)
Stride Tremor Accumulated (Windowed Lateral Tremor Intensity)
Stride Fluidity Accumulated (Windowed Total Tremor Intensity)
Swing Time Right Foot (msec)
Swing Time Left Foot (msec)
Stance Phase Right Foot (msec)
Stance Phase Left Foot (msec)
Asymmetry Factor Stance Phase Right/Left Stance Phase (Stance Phase Right-Stance Phase Left)
Double Support Stance Time (msec)
Vertical Displacement [Mid-Stance] Max (cm)
Vertical Displacement [Double Support] Min (cm)
Heel Strike Time Right Foot (msec)
Heel Strike Time Left Foot (msec)
Heel Strike Pressure Right Foot (shift N - Newton)
Heel Strike Pressure Left Foot (N)
Asymmetry Factor Right/Left Heel Strike Pressure (Heel Strike Pressure Right Foot - Heel Strike Pressure Left Foot)
Distance Travelled Accumulated (meters - m)
Average Velocity (m/min)
Variability of each of the factors The system described herein provides the capability to "gate" or provide a "window" with respect to the patient biomechanical data. Gating of the biomechanical data is useful for repetitive patient movements, such as the repetitive strides while a patient is walking. Sensor data, from one or more sources, such as pressure sensors, IMU sensors, video data, and EMG data, is used to identify cycles of movement that repeat over time. For example, when a patient walks, foot pressure increases and decreases repetitively, as the patient's foot contacts the ground and then is lifted off the ground. Likewise, the velocity of the foot increase as the foot moves forward and decreases to zero while the foot is planted on the ground. As a further example, the Y-position or height of the patient's foot cycles between a low position (on the ground) and a high position (approximately in mid stride). The "gating" technique identifies repeating cycles or "windows" within such data. In the case of a patient walking, the cycle is repeated with each step. Although there may be variations between cycles, e.g., between steps, certain patterns repeat with each cycle. Selecting an onset time (start time) of each cycle involves locating an identifiable point (maximum or minimum) of a biomechanical parameter. The selection of the parameter for the onset time is selected based upon the available data. Thus, in some embodiments, the moment when the heel-strike pressure exceeds a threshold may be used to demarcate the onset time of each cycle. (See, e.g., FIG. 5. Pressure 316a and 316b includes a cyclic characteristic. "Onset" may be determined at the moment the pressure exceeds a threshold.) Similarly, the onset time may be demarcated when foot velocity falls to zero.

In some embodiments, raw frames data is pre-processed, taking the instant data and "gating" it, e.g., identifying a window, and then analyzing data within that window to identify outliers and to perform analysis on the data, e.g., exponential analysis, averaging data among multiple windows. Fusion of sensor data, by including both IMU data and heel-strike pressure data, allows for more precise identification of onset times for a single stride or other repeated units of motion than using data from a single sensor. Sensor data captured within a single stride is considered a "window," and information extracted from this analysis includes, e.g., stride length, step count, cadence, time when step occurs, distance traveled, stance phase/swing phase, double support time, velocity, symmetry analysis (e.g., between left and right leg), outward swing, shuffling, power vector, lateral acceleration, step width, variability of each of these dimensions, additional parameters derived from the above-described information, etc. Feature extraction can be processed on microprocessor chip, e.g., a 32-bit chip. Capture of wireless synchronous-gated biomechanical sensor data and video data capture capability allows for time-series template creation.

The data can be indexed by the patient or the therapist during a music therapy session. The "gating" functionality described above is useful to tie exception conditions to particular strides or steps. For example, the therapist may observe a particular exception condition or behavior (such as an anomaly or incident) in the patient's movement. The indexing function allows the therapist to initiate, such as, capture to "record," an exception condition or behavior via a user interface on the handheld tablet or laptop, such as the wireless trigger unit 250 illustrated in FIG. 4, or voice control. A notation can be created that includes a timestamp and a comment, such as the occurrence of a "stumble" by the patient while walking. Such indexing facilitates time-series template creation. These time-series templates will be studied for review of therapy session events and for the development of times-series templates for training machine learning algorithms such as non-linear multi-layered perceptrons (NLMLP), convolutional neural networks (CNNs), and recurrent neural networks (RNNs) with long short term memory (LSTM).

In one embodiment, a communication protocol is provided to transfer sensor data from edge processing 104 (e.g. at the sensors 200) to the collector 106. See Table 4 below. In some embodiments, if the connection is idle for more than 100 ms, the RF has timed out.

TABLE 4

| [0x10] | Start of frame |
|---|---|
| [0x49] | FootClipSensor ID = 'I' |
| [0x52] or [0x4C] | Which FootClipSensor = 'R' or 'L' |
| [0x00~0xFF] | Zone 1 |
| [0x00~0xFF] | Zone 2 |
| [0x00~0xFF] | Zone 3 |
| [0x00~0xFF] | Zone 4 |
| [Az] | Az |
| [Ay] | Ay |
| [Ax] | Ax |
| [HighByteSeqNum] | High Byte Sequence |
| [LowByteSeqNum] | Low Byte Sequence |

In one embodiment, the foot pressure sensor zone scanning is performed by the FootScan routine where the FootDataBufferIndex is initialized and the foot pressure sensor zone is activated by enabling MCU direction mode for output [PTCDD_PTCDDN=Output] and bringing the associated port line low [PTCD_PTCD6=0]. As the foot pressure sensor zone is activated based on the foot pressure sensor zone scanning map, the foot pressure sensor zones attached to the MCU analog signal ports will be sampled and then the current voltage reading converts them into digital form (which is the—time zone foot pressure).

Several variables such as FootDataBufferIndex and IMUBufferIndex are used to prepare the IEEE 802.15.4 RF packets gsTxPacket.gau8TxDataBuffer[ ] which are for sending the data to be used in FootDataBuffer[ ] and IMUBuffer[ ]. The RF packets are sent using the RFSendRequest(&gsTxPacket) routine. This routine checks to see if gu8RTxMode is set at IDLE_MODE and uses gsTxPacket as a pointer to call the RAMDrvWriteTx routine which then calls SPIDrvRead to read the RF transceiver's TX packet length register contents. Using these contents, mask length settings update and then add 2 for CRC and 2 for code bytes.

SPISendChar is called to send a 0x7E byte, which is the 2nd code byte and then the SPIWaitTransferDone is called again to verify the send is done. With these code bytes sent, then the rest of the packet is sent using a for loop, where psTxPkt→u8DataLength+1 are the number of iterations to a series of sequential to SPISendChar, SPIWaitTransferDone, SPIClearRecieveDataReg. When complete, the RF transceiver is loaded with the packet to send. The ANTENNA_SWITCH is set to transmit, the LNA_ON mode enabled, and finally a RTXENAssert call made to actually send the packet.

Collector

The primary function of the collector 106 is to capture data from the edge processing 104, transfer data to and receive processed data from the analytics system 108, and transfer data to the music therapy center 110, described below. In some embodiments, the collector 106 provides control functionality, e.g., a user interface to login, configure the system, and interact with users, and includes a display unit to visualize/display data. The collector 106 may include lightweight analytics or machine learned algorithms for classification (e.g., lateral tremor, asymmetry, instability, etc).

The collector 106 receives body, motion, and localization data from the edge processor 104. Data received at collector 106 can be raw or processed at the edge 104 prior to transfer to the collector. For example, the collector 106 receives fused sensor data, subject to "windowing" and feature extraction. The transferred data can include two levels of data: (1) RF Packets sent from the Right/Left foot sensors as described in Table 1, (2) RF Packets from the Right/Left foot sensors which contains higher level attributes and features as described in Tables 2 and 3. The collector 106 locally stores the data. In some embodiments, the collector 106 classifies movement from the received data, e.g., comparing it to models stored locally (pre-downloaded from the analytics system) or sent to analytics system for classification. The collector may include a display unit to visualize/display the data.

In some embodiments the collector 106 operates on a local computer that includes a memory, a processor and a display. Exemplary devices on which the collector is installed can include AR devices, VR devices, tablets, mobile devices, laptop computers, desktop computers, and the like. FIG. 2 illustrates a handheld device 220 having a display 222, and which performs the collector functions. In some embodiments, the connection parameters for transferring data between the patient sensor and the collector are made include the use of Device Manager in Windows (e.g., Baud rate: 38400, data bits: 8; parity: none, stop bits: 1). In some embodiments, the collector 106 includes a processor that is held or worn by the music therapy patient. In some embodiments, the collector 106 includes a processor that is remote from the music therapy patient and carried by a therapist, and connected wirelessly or via a wired connection to the music therapy patient.

In one embodiment, a foot pressure/6-degrees of freedom motion collecting node captures RF transmitted data packets containing real-time foot pressure/6-degrees of freedom motion profile data from the foot pressure/6-degrees of freedom motion capture device. This is started by the foot pressure/6-degrees of freedom motion collecting node which creates a RF packet receive queue that is driven by a call back function on RF transceiver packet receive interrupts.

When an RF packet is received from a foot pressure/6-degrees of freedom motion capture device 200, a check is first made to determine if this from a new foot pressure/6-degrees of freedom motion capture device or an existing one. If this is from an existing foot pressure/6-degrees of freedom motion capture device, RF packet sequence numbers are checked to determine continuous synchronization before further analyzing the packet. If this is a foot pressure capturing/6-degrees of freedom motion device, a foot pressure/6-degrees of freedom motion capture device context state block is created and initialized. The context state block includes information, e.g., the foot pressure profile, [what additional information?]

Above this RF packet session level process for node to node communication, is the analysis of the RF packet data payload. This payload contains the foot pressure profile based on the current variable pressure following the 6-degrees of freedom motion. This is structured as follows: | 0x10| start|F1| F2| F3| F4|$A_x$| $A_y$| $A_z$| Pi| Yi| Ri| XOR checksum|.

The IEEE 802.15.4 standard specifies a maximum packet size of 127 bytes and the Time Synchronized Mesh Protocol (TSMP) reserves 47 Bytes for operation, leaving 80 Bytes for payload. The IEEE 802.15.4 is compliant with the 2.4 GHz Industrial, Scientific, and Medical (ISM) band Radio Frequency (RF) transceiver.

The RF module contains a complete 802.15.4 Physical layer (PHY) modem designed for the IEEE 802.15.4 wireless standard which supports peer-to-peer, star, and mesh networking. It is combined with a MCU to create the required wireless RF data link and network. The IEEE 802.15.4 transceiver supports 250 kbps O-QPSK data in 5.0 MHz channels and full spread-spectrum encode and decode.

In some embodiments, control, reading of status, writing of data, and reading of data is done through the sensing system node device's RF transceiver interface port. The sensing system node device's MPU accesses the sensing system node device's RF transceiver through interface 'transactions' in which multiple bursts of byte-long data are transmitted on the interface bus. Each transaction is three or more bursts long, depending on the transaction type. Transactions are always read accesses or write accesses to register addresses. The associated data for any single register access is always 16 bits in length.

In some embodiments, control of the foot pressure/6-degrees of freedom motion collecting node's RF transceiver and data transfers are accomplished by means of a Serial Peripheral Interface (SPI). Although the normal SPI protocol is based on 8-bit transfers, the foot pressure/6-degrees of freedom motion collecting collector node's RF transceiver imposes a higher level transaction protocol that is based on multiple 8-bit transfers per transaction. A singular SPI read or write transaction consists of an 8-bit header transfer followed by two 8-bit data transfers.

The header denotes access type and register address. The following bytes are read or write data. The SPI also supports recursive 'data burst' transactions in which additional data transfers can occur. The recursive mode is primarily intended for Packet RAM access and fast configuration of the foot pressure/6-degrees of freedom motion collecting node's RF In some embodiments, all foot pressure sensor zones are sequentially scanned and the entire process repeats until a reset condition or inactivity power-down mode. The 6-degrees of freedom motion is captured by a serial UART interface to the Inertial Measurement Unit (IMU) from the MCU. The sampling rate for all sensing dimensions is 100-300 Hz which is $A_x$, $A_y$, $A_z$, Pitch, Yaw, Roll and which sampled data is stored in IMUBuffer[ ].

A call is made to SPIDryWrite to update the TX packet length field. Next, a call to SPIClearRecieveStatReg is made to clear the status register followed by a call to SPIClearRecieveDataReg to clear the receive data register to make the SPI interface ready for reading or writing. With the SPI interface ready, a call is made to SPISendChar sending a 0xFF character which represents the 1st code byte and then SPIWaitTransferDone is called to verify the send is done.

Figure 5:
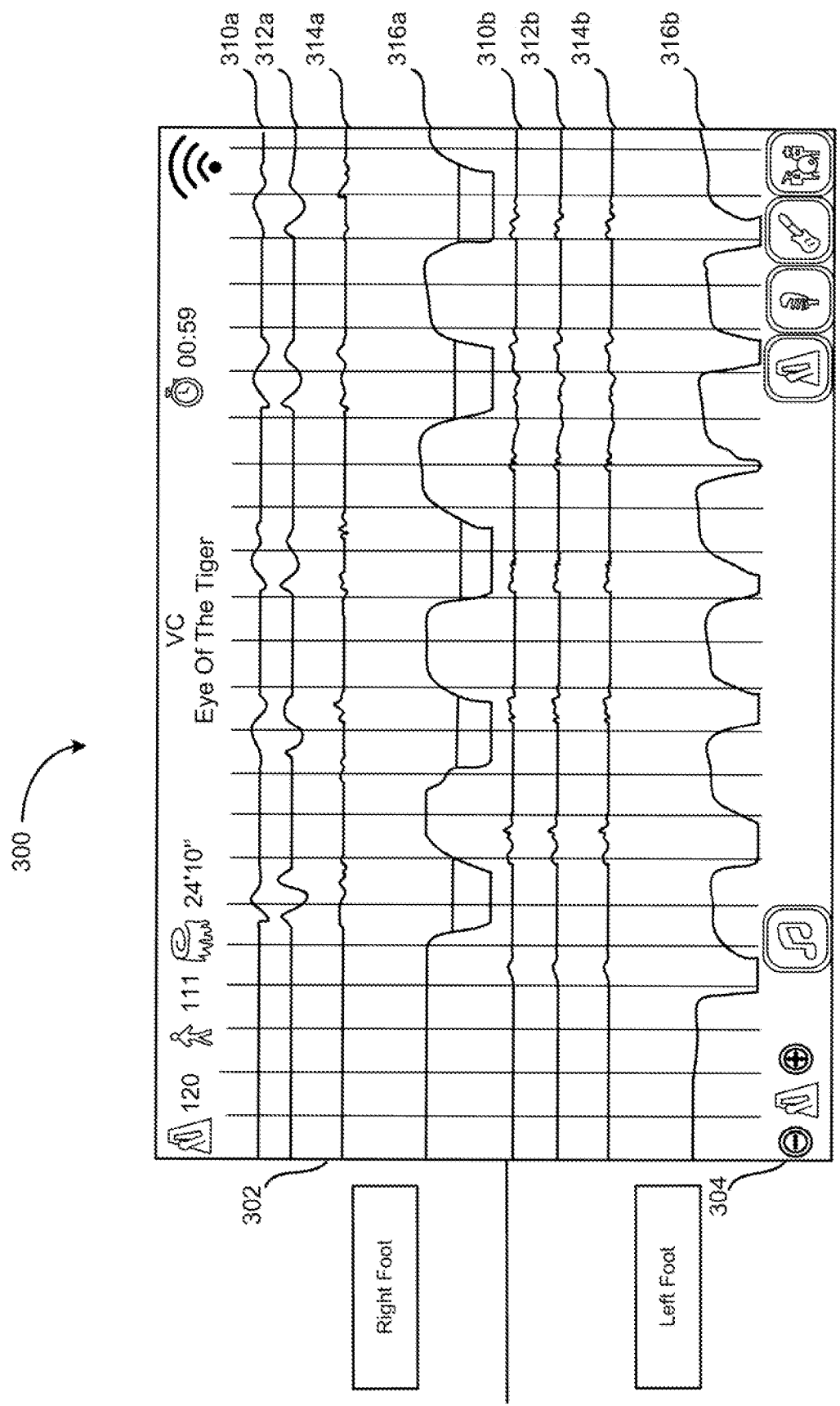
FIG. 5 illustrates an exemplary display of a component of a system for rehabilitation of a user by providing music therapy in accordance with exemplary embodiments of the disclosed subject matter.

FIG. 5 is an exemplary output 300 that may be provided on display 222 of the handheld device. For example, when therapy is provided for a patient's gait, the display output 300 may include a portion for the right foot 302 and a portion for the left foot 304. As a function of time, the display for the right foot includes accelerations $A_x$ 310*a*, $A_y$ 312*a*, and $A_z$ 314*a*, and foot pressure 316*a*. Similarly, the display for the left foot includes acceleration $A_x$ 310*a*, $A_y$ 312*a*, and $A_z$ 314*a*, and foot pressure 316*a*.

Classification is understood as the correlation of data, e.g., sensor fused data, feature data, or attribute data to real world events, e.g., activities or disposition of the patient. Typically, the classification is created and performed on the analytics system 108. In some embodiments, the collector 106 has a local copy of some 'templates.' Thus, the incoming sensor data and feature extracted data can be classified at the collector or the analytics system.

Context refers to the circumstances or facts that form the setting for an event, statement, situation, or idea. Context-aware algorithms examine the "who," "what," "when" and "where" related to the environment and time in which the algorithm is executed against certain data. Some context-aware actions include an identity, location, time, and activity being executed. In using contextual information to formulate a deterministic action, context interfaces occur among the patient, the environment, and the music therapy session.

The patient's reaction context to a music therapy session can involve a layer of algorithms that interpret the fused sensor data to infer higher-level information. These algorithms distill the patient reaction context. For example, a patient's bio-mechanical gait sequence is analyzed as it relates to a specific portion of the music therapy session. In one example, "lateral tremor" is the classifier of interest. Accordingly, it is determined that the patient's gait becomes more fluid with less lateral tremor.

Analytics Systems

The analytics systems 108, sometimes referred to as the back end system, store large models/archives and include machine learning/analytics processing, with the models described herein. In some embodiments, a web interface for login to view archived data, and a dashboard is also provided. In some embodiments the analytics system 108 is located on a remote server computer which receives data from the collector 106 running on a handheld unit such as handheld device or tablet 220. It is contemplated that the processing capability needed to perform the analytics and machine learning functions of the analytics system 108 may be also located on the handheld device 220.

Figure 6:
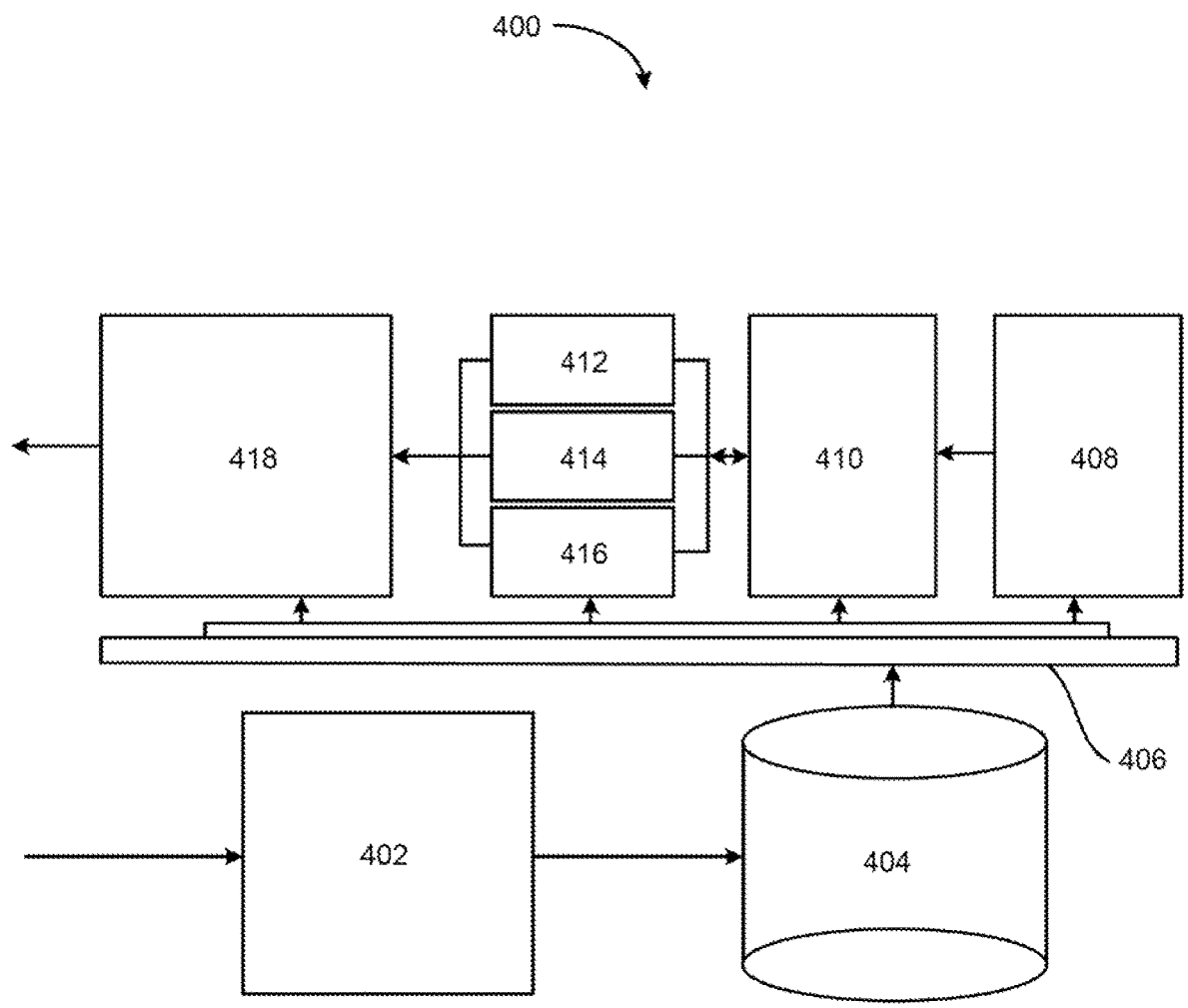
FIG. 6 is a flow diagram for one implementation of an analytics process in accordance with exemplary embodiments of the disclosed subject matter.

Data is transferred from the collector 106 to the analytics systems 108 for analytics processing. As illustrated in FIG. 6, the analytics processing 400 includes a user-interface 402 for receiving data from the collector 106. A database storage 404 receives incoming data from the collector 106 for storage. Training data as well as outputs of the analytics processing, e.g., the ensemble machine learning system 410, may also be stored on storage 404 to facilitate the creation and refinement of the predictive models and classifiers. A data bus 406 allows flow of data through the analytics processing. A training process 408 is performed on training data to derive one or more predictive models. An ensemble machine learning system 410 utilizes the predictive models. The output of the ensemble machine learning system 410 is an aggregation of these predictive models. This aggregated output is also used for classification requirements with template classifiers 412, such as tremor, symmetry, fluidity, or learned biomechanical parameters such as entrainment, initiation, etc. An API 418 connects to the collector and/or music therapy Center. Therapy algorithms 414 and predictive algorithms 416 include multi-layer perceptron neural networks, hidden Markov models, Radal based function networks, Bayesian inference models, etc.

An exemplary application of the systems and methods described herein is analysis of a patient's bio-mechanical gait. The gait sequence is feature-extracted into a series of characteristic features. The presence of these and other features in captured sensor-fused data inform the context detection algorithm if the patient's bio-mechanical gait sequence is valid. Bio-mechanical gait sequence capture requires robust context detection, which is then abstracted over a representative population of music therapy patients.

An example of such an activity is the location of a patient at an instance in time and their response to the music therapy at that time. The recognition and correlation of patient music therapy responses allows for recognition specific patterns of music therapy patient responses. Specific music therapy regimes are then benchmarked and analyzed for performance and efficacy by creating a baseline of music therapy patient responses and correlating them to future music therapy patient responses.

In combination with motion sensing, a distance metric with gait bio-mechanics capture is used to determine patient path trajectory using temporal and spatial variations/deviations between two or more music therapy sessions. From this sensor-fused data capture, features are extracted and classified to label various key patient therapy responses. Further sensor-fused data analysis uses histograms to allow for initial music therapy response pattern detection.

For music therapy session sensor fused data analysis, initially, patient specific Bayesian inference models are used utilizing Markov chains. The states of the chain represent the patient specific response patterns captured from music therapy baseline sessions. The inference is based on knowledge of the patient response pattern appearances at each sample interval and the temporal link to the previous state.

The prediction routine, a Multi-Layer Perceptron Neural Network (MLPNN), uses a directed graph node-based model having a top layer root-node which predicts requirements for reaching a subsequent node and obtaining a patient's sensor-fused data feature vector. This sensor fused data feature vector contains time-series processed motion data, music signature data, and video image data that is specifically significant for further processing. The directed graph, in this case, look like trees that are drawn upside down, where the leaves are at the bottom of the tree and the roots are the root-node. From each node, the routine can go to the left, where left is the left node on the next layer below the top layer which is where the root-node is located, selecting the left sub-node as the next observed node, or to the right where right is the right node on the next layer below the top layer where the root-node is located, and this based on the value of a certain variable whose index is stored in the observed node. If the value is less than the threshold, the routine goes to the left node and if greater, it goes to the right node. These regions, here, left & right, become the predictor spaces.

The model uses two types of input variables: ordered variables and categorical variables. An ordered variable is a value that is compared with a threshold that is also stored in a node. A categorical variable is a discrete value that is tested to see whether it belongs to a certain limited subset of values and stored in a node. This can be applied to various classifications. For example, mild, medium, and severe can be used to describe tremor and is an example of a categorical variable. Conversely, a fine grained range of values or a numerical scale, can be used to similarly describe tremor but in a numerical fashion.

If the categorical variable belongs to the limited set of values, the routine goes to the left node and if not, it goes to the right node. In each node, a pair of entities: variable_index, decision_rule (threshold/subset) are used to make this decision. This pair is called a split which splits on the variable: variable_index.

Once a node is reached, the value assigned to this node is used as the output of the prediction routine. The Multi-Layer Perceptron Neural Network is built recursively, starting from the root node. All training data, feature vectors, and responses, are used to split the root node, as described earlier; where the entities: variable_index, decision_rule (threshold/subset) segments the prediction regions. In each node the optimum decision rule on the best primary split is found based on gini "purity" criteria for classification and sum of squared errors for regression. The gini index is based on the measure of total variance across a set classes. The gini "purity" criteria referrers to a small gini index value, indicating that a node contains predominantly observations from a single class, which is the desired state.

Once the Multi-Layer Perceptron Neural Network is built, it may be pruned using a cross-validation routine. To avoid model over-fitting, some of the branches of the tree are cut off. This routine may be applied to standalone decisions. One salient property of the decision algorithm (MLPNN), described above, is an ability to compute the relative decisive power and importance of each variable.

The variable importance rating is used to determine the most frequent interaction type for a patient interaction feature vector. The pattern recognition starts with the definition of a decision space suitable to discriminate different categories of music therapy responses and music therapy events. A decision space can be represented by a graph with N dimensions, where N is the number of attributes or measurements considered to represent the music therapy responses and music therapy events. The N attributes compose a feature vector or signature which can be plotted in the graph. After sufficient samples have been inputted, the decision space reveals clusters of music therapy responses and music therapy events belonging to different categories which is used to associate new vectors to these clusters.

The dynamic closed-loop rehabilitation platform music therapy system utilizes several deep learning neural networks for learning and recalling patterns. In one embodiment, a non-linear decision space is built using the adaptive Radial Basis Function (RBF) model generator. New vectors can be calculated using the RBF model and/or with a K-Nearest Neighbor classifier. FIG. 6 illustrates the workflow of the machine learning sub-system of the dynamic closed-loop rehabilitation platform music therapy system.

Figure 7:
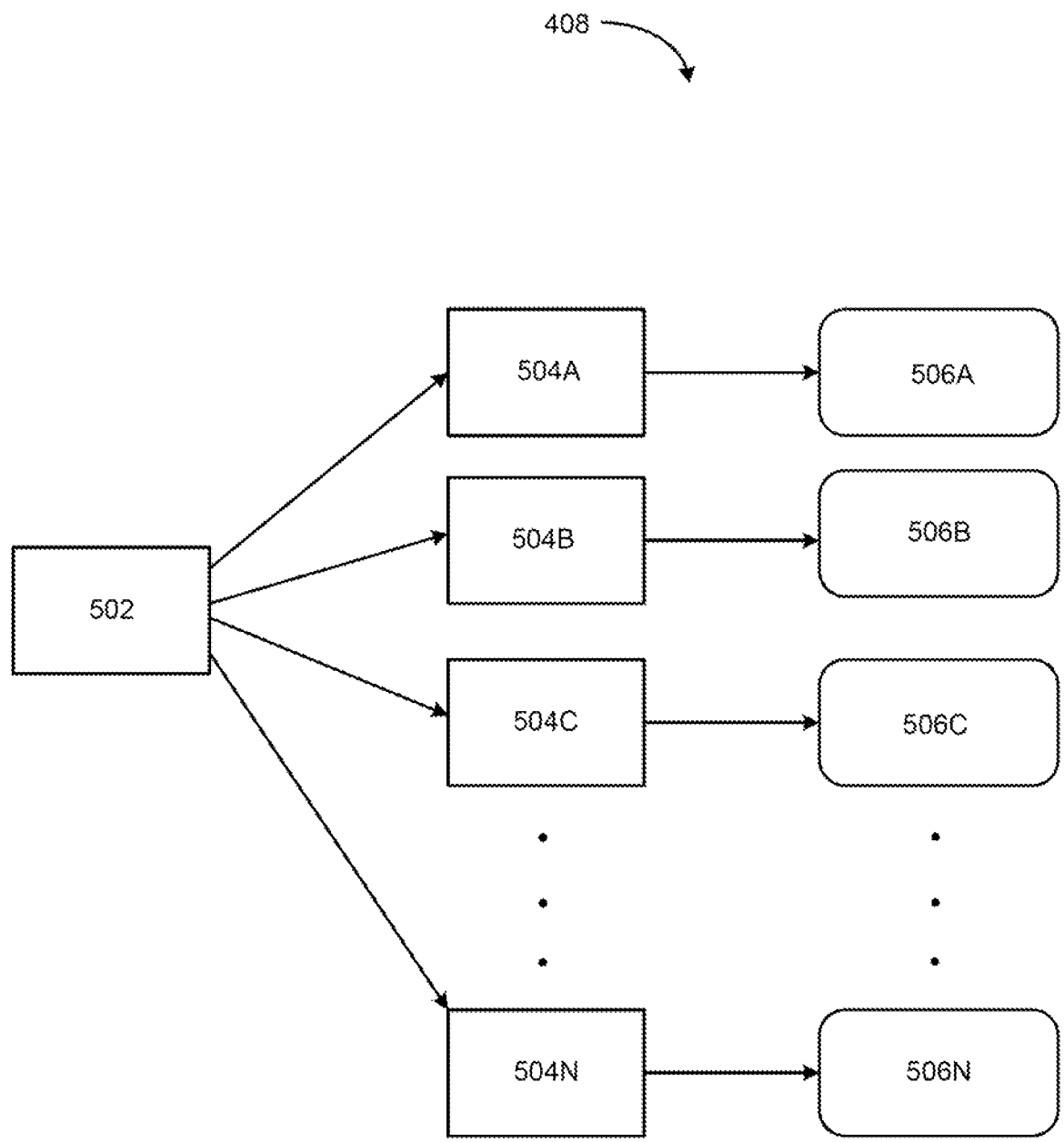
FIGS. 7-10 are flow diagrams for one implementation of a process in accordance with exemplary embodiments of the disclosed subject matter.

FIG. 7 illustrates the supervised training process 408, which includes a number of training samples 502, e.g., inputs would be features such as described in Table 3, above and example outputs will be items such as tremor, asymmetry, and power, the degree of these items, the prediction of changes, classification of how well the patient is recovering. It is understood new outputs are learned as a part of this process. This provides a base for higher levels of abstractions of the predictions and classifications as it is applied to different use cases (e.g. different disease states, combinations with pharmaceuticals, notifications to providers, fitness, and fall prevention). These training samples 502 are run with learning algorithms A1 504a, A2 504b, A3 504c . . . AN 504n to derive predictive models in M1 506a, M2 506b, M3 506c . . . MN 506n. Exemplary algorithms include Multi-Layer Perceptron Neural Networks, Hidden Markov Models, Radal Based Function Networks, Bayesian inference models.

Figure 8:
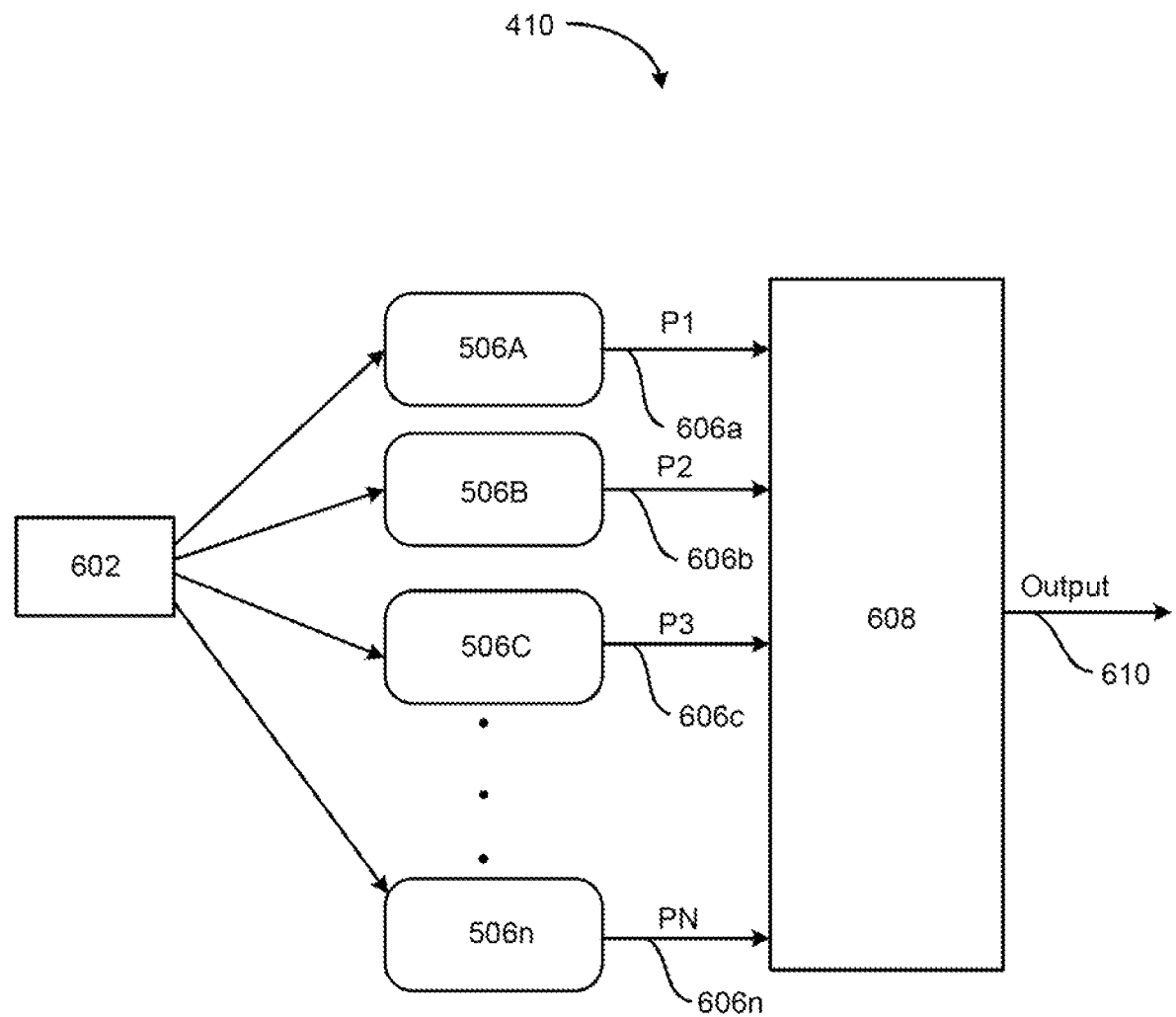

FIG. 8 illustrates the ensemble machine learning system 410, as an aggregation of the predictive models M1 506a, M2 506b, M3 506c . . . MN 506n on sample data 602 e.g., feature extracted data, to provide multiple predictive outcome data 606a, 606b, 606b . . . 606n. An aggregation layer 608, e.g., including decision rules and voting, is used to derive the output 610, given a plurality of predictive models.

The MR ConvNet system has two layers, where the first layer is a convolutional layer with mean pooling support. The MR ConvNet system second layer is a fully connected layer that supports multinomial logistic regression. Multinomial logistic regression, also called Softmax, is a generalization of logistic regression for handling multiple classes. In the case of logistic regression, the labels are binary.

Figure 9:
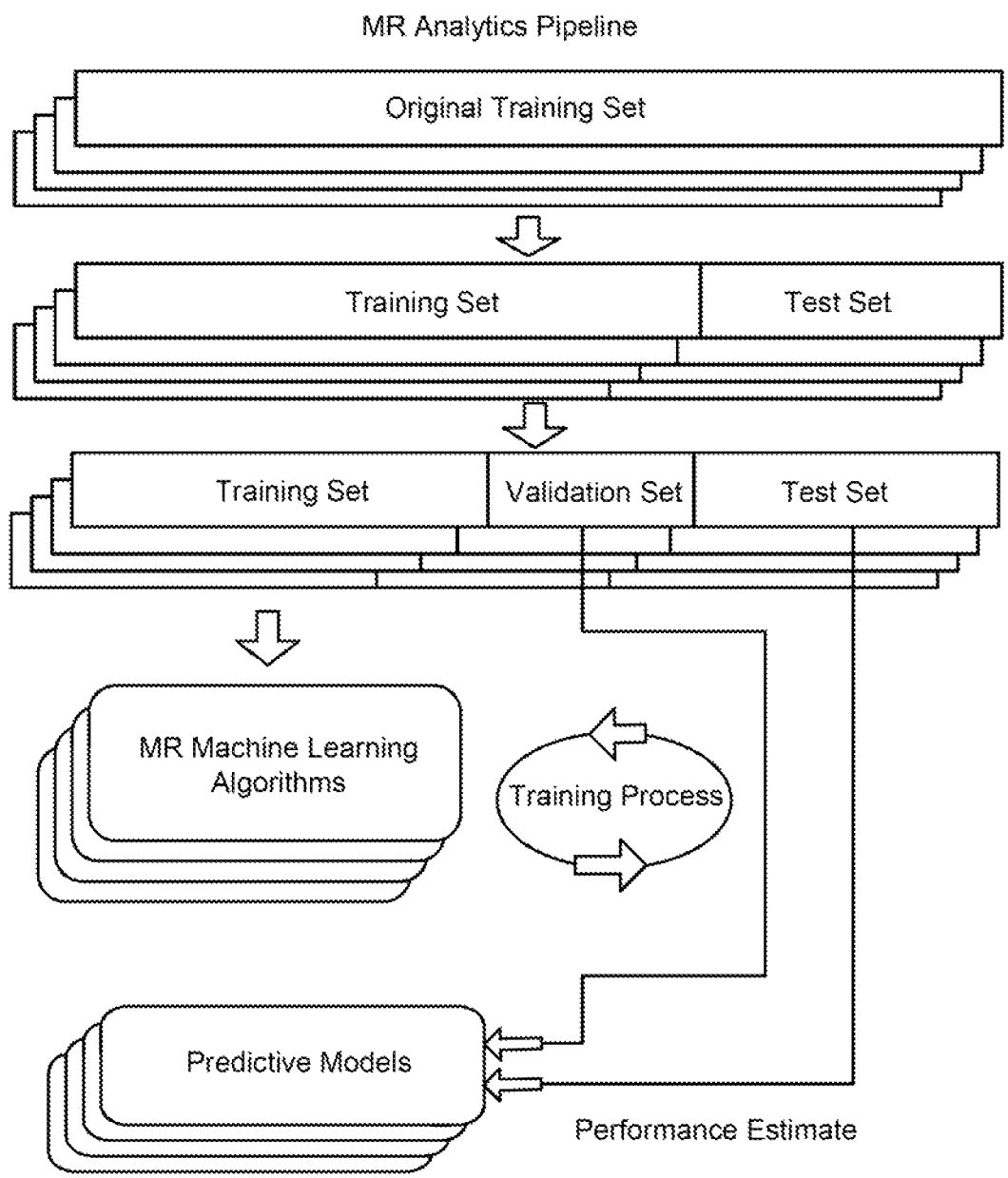

Softmax is a model that is used to predict the probabilities of the different possible outputs. The following assumes a multiclass classifier with m discrete classes via a Softmax final output layer:

$$Y1 = \text{Softmax}(W11*X1 + W12*X2 + W13*X3 + B1) \quad [1]$$

$$Y2 = \text{Softmax}(W21*X1 + W22*X2 + W23*X3 + B2) \quad [2]$$

$$Y3 = \text{Softmax}(W31*X1 + W32*X2 + W33*X3 + B3) \quad [3]$$

$$Ym = \text{Softmax}(Wm1*X1 + Wm2*X2 + Wm3*X3 + Bm) \quad [4]$$

$$\text{In general: } Y = \text{softmax}(W*X + B) \quad [5]$$

$$\text{Softmax}(X)i = \exp(Xi)/\text{Sum of } \exp(Xj) \text{ from } j=1 \text{ thru } N \quad [6]$$

Where Y=Classifier output; X=Sample input (all scaled (normalized) feature values); W=Weight Matrix. The classifications will, for example, score asymmetry, such as "Moderate Asymmetry score 6 out of 10 (10 high level of asymmetry to 0 for no asymmetry)" or gait fluidity "Gait Fluidity score 8 out of 10 Normal", etc. The Analytics pipelines is illustrated in FIG. 9.

Softmax regression allows for handling multiple classes beyond two. For logistic regression: $P(x)=1/(1+\exp(-Wx))$ where W contains the model parameters that were trained to minimize a cost function. Also, x is the input features vector and $$((x(1), Y(1)), \ldots, (x(i), Y(i))) \quad [7]$$

would represent the training set. For multi-class classification, Softmax regression is used where y can take on N different values representing the classes instead of 1 and 0 in the binary case. So for the training set $((x(1), y(1)), \ldots, (x(i), y(i)))$, y(n) can be any value in the range of 1 through N classes.

Next, $p(y=N|x;W)$ is the probability for each value of $i=1, \ldots, N$. The following mathematically illustrates the Softmax regression process:

$$Y(x) = (p(y=1|x;W), p(y=2|x;W), \ldots p(y=N|x;W)) \quad [8]$$

Where Y(x) is the answer to the hypothesis, that given the input x, output the probability distribution across all classes such that their normalized sum is 1.

The MR ConvNet system convolves every windowed biomechanical data frames, as a vector, with every biomechanical template filter, as a vector, and then generates the responses using a mean pool function which averages the feature responses. The convolution process computes Wx while adding any biases and then passes this to a logistic regression (sigmoid) function.

Next, in the MR ConvNet system's second layer, the sub-sampled biomechanical template filter responses are moved into a two dimensional matrix where each column represents the windowed biomechanical data frames as a vector. The Softmax regression activation process is now initiated using:

$$Y(x) = (1/(\exp(Wx) + \exp(Wx) + \ldots + \exp(Wx)) * (\exp(Wx), \exp(Wx), \ldots, (\exp(Wx)) \quad [9]$$

The MR ConvNet system is trained with an optimization algorithm, gradient descent where a cost function J(W) is define and will be minimized:

$$J(W) = 1/j*((H(t(j=1), p(y=1|x;W) + H(t(j=2), p(y=2|x; W) + \ldots + H(t(j), p(y=N|x;W)) \quad [10]$$

Where t(j) are the target classes. This averages all cross-entropies over the j training samples. The cross-entropy function is:

$$H(t(j),p(y=N|x;W)-t(j=1)*\log(p(y=1|x;W))+ \\ t(j=2)*\log(p(y=2|x;W))+ \ldots +t(j)*p(y=N|x;W) \quad [11]$$

Figure 10:
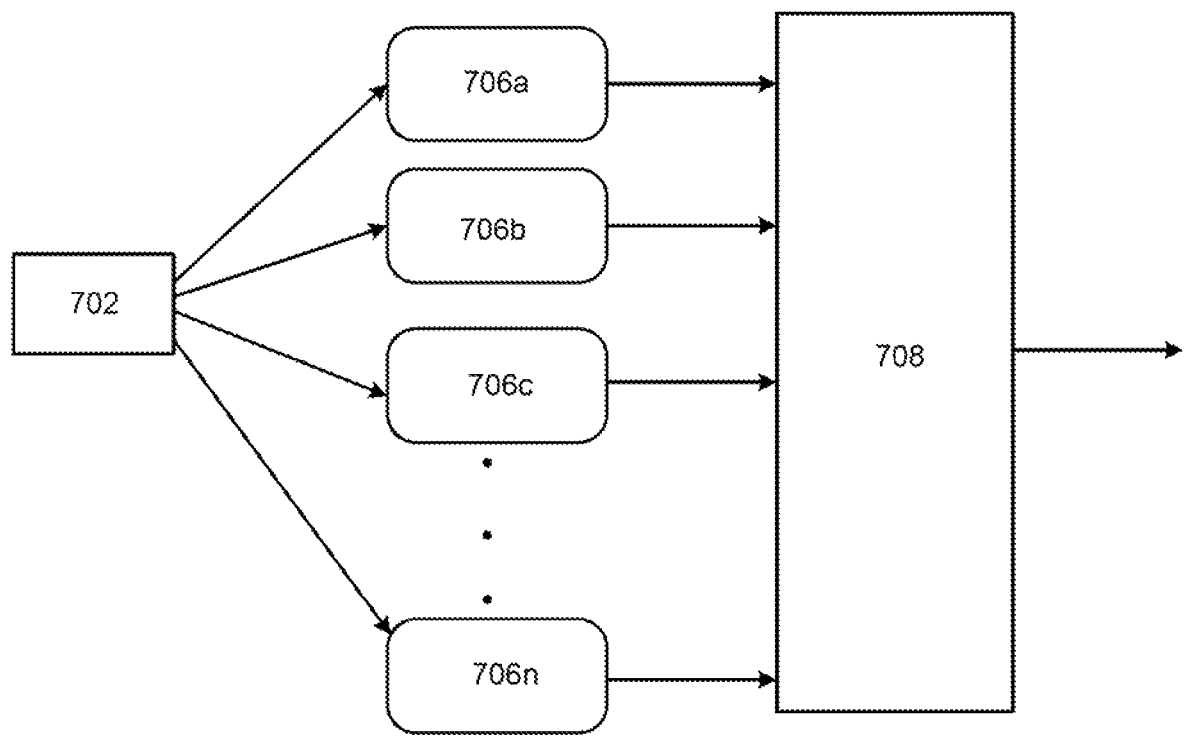

In FIG. 10, the ensemble machine learning system 408 includes a plurality of predictive models, e.g., Template Series 1 (tremor) 706a, Template Series 2, (symmetry) 706b, Template Series 3 (fluidity) 706c . . . additional templates (other learned biomechanical parameters, e.g., entrainment, initiation, etc.) 706n which are applied to conditioned inputs 702, e.g., for example, it could be the following: stride length for right and left features (x1, x2), variance of stride length right and left features (x3, x4), cadence right and left features (x6,x7), variance of cadence right and left features (x8, x9) etc. . . . this is where sample (x1,x2, . . . xn) are referred to as the Vector X which is input to 702 in the ensemble of ML algorithms. These are conditioned referencing normalized and/or scaled inputs]. The aggregation classifier 708 outputs such information as tremor scale, symmetry scale, fluidity scale, etc.

Music Therapy Center

The music therapy center 110 is the decision making system that runs on processor, such as handheld device or laptop computer 220 of FIG. 2. The music therapy center 110 takes the inputs from the feature-in extracted sensor data at the collector 106, compares them to the defined process for the delivering of the therapy, and then delivers content of auditory stimuli that is played through music delivery system 230.

Embodiments of the invention use contextual information to determine why a situation is happening, then encodes observed actions, which causes a dynamic and modulated change in the system-state, and thus the music therapy session, in a closed-loop manner.

The interactions between the patient and music therapy session provide real-time data for determining music therapy patient context awareness, including motion, posture, strides, and gait reaction. After input data is collected by the sensing nodes (at the sensors), embedded nodes process the context-aware data (at edge processing), and provide immediate dynamic action and/or transmit the data to the analytics systems 108, e.g., an elastic network-based processing cloud environment for storage and further processing and analysis.

Based on inputs, the program will take any existing song content, alter the cadence, major/minor chords, meter and musical cues (e.g., melodic, harmonic, rhythmic and force cues). The system can overlay a metronome on existing songs. The song content can be beat mapped (e.g., if W in response to AV or MP3 file) or in MIDI format so that the precise knowledge of when the beat occurs can be used to calculate the entrainment potential. The sensors on the patient can be configured to provide haptic/vibration feedback pulsing at the music content.

EXAMPLES

Figure 11:
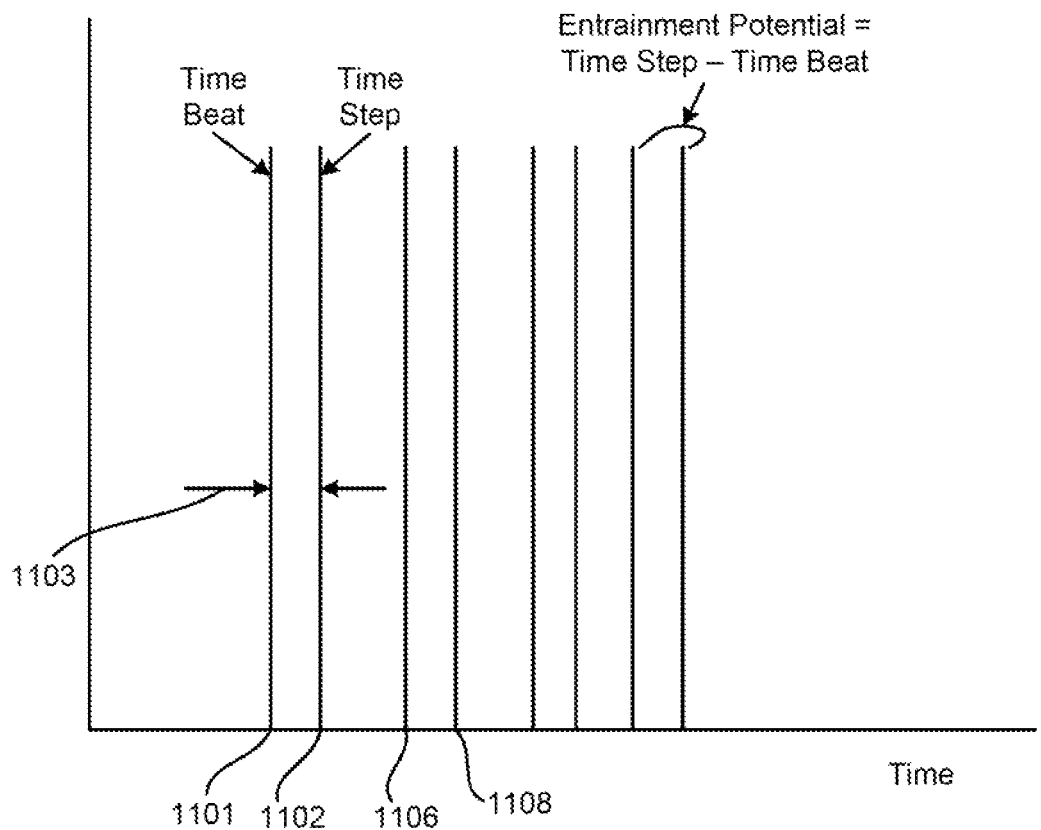
FIG. 11 is a time plot illustrating music and physical movement of the patient in accordance with exemplary embodiments of the disclosed subject matter.

An exemplary application of the method is described herein. Gait training analyzes the real-time relationship between the beats of the music being played for the patient and the individual steps taken by the patient in response to those particular beats of music. As discussed above, gating analysis is used to determine a window of data that repeats, with some variation, with each step or repetitive movement. In some embodiments, the beginning of the window is determined as the time when the heel strike pressure exceeds a threshold (or other sensor parameter.) FIG. 11 is an exemplary time plot illustrating the respective output times (also referred to as beat times) for beats of music, "time beats," and the steps taken by the patient, "time step." Thus the onset time in this case is associated with the "time step." In particular, the plot illustrates a time beat 1101 of the music at time Time Beat 1. After a duration of time, the patient takes a step in response to time beat 1001, i.e., time step 1102, at time Time Step 1. The entrainment potential 1103 represents the delay (if any) between Time Beat 1 and Time Step 1.

Figure 12:
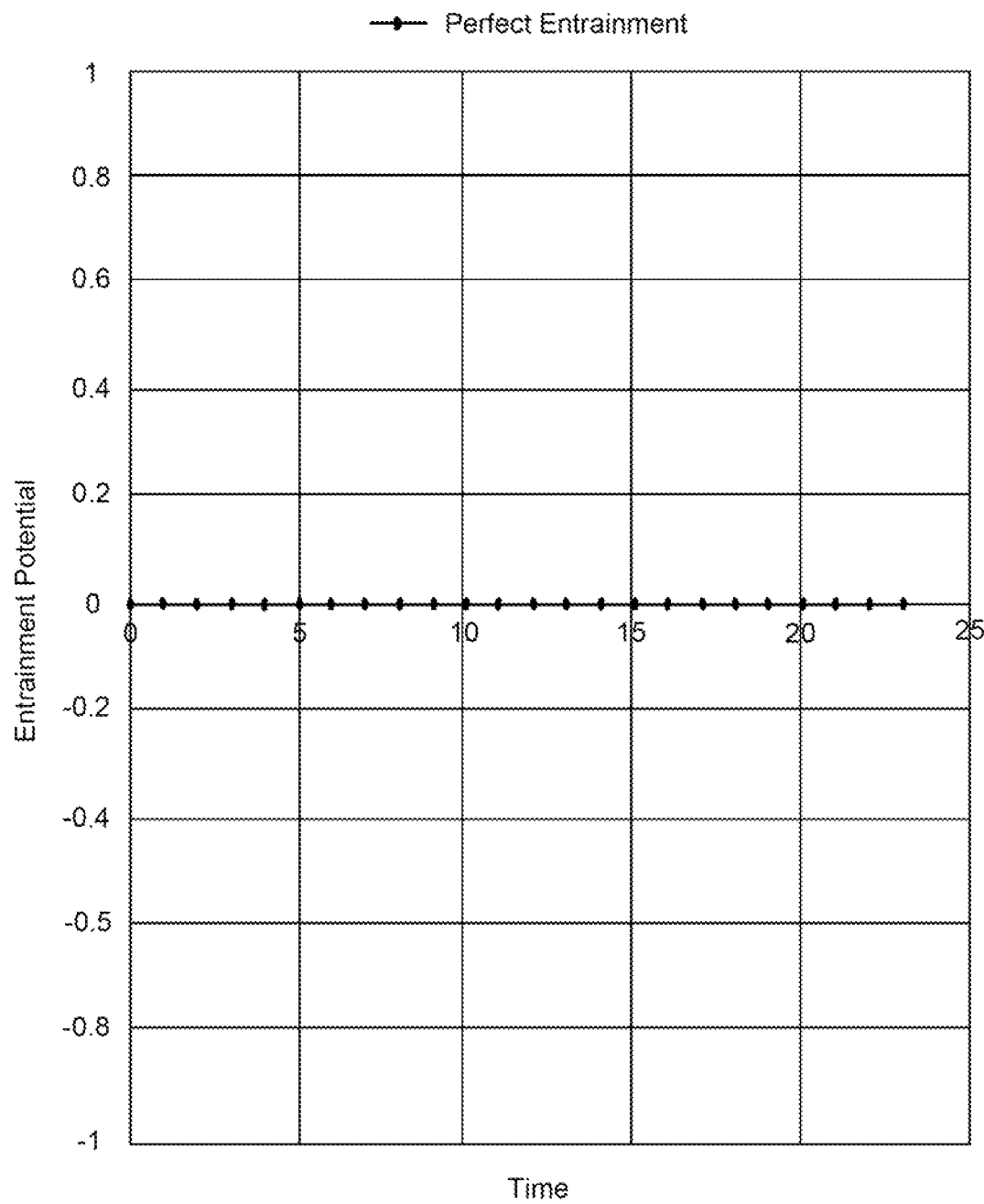
FIGS. 12-13 illustrate a patient response in accordance with exemplary embodiments of the disclosed subject matter.
Figure 13:
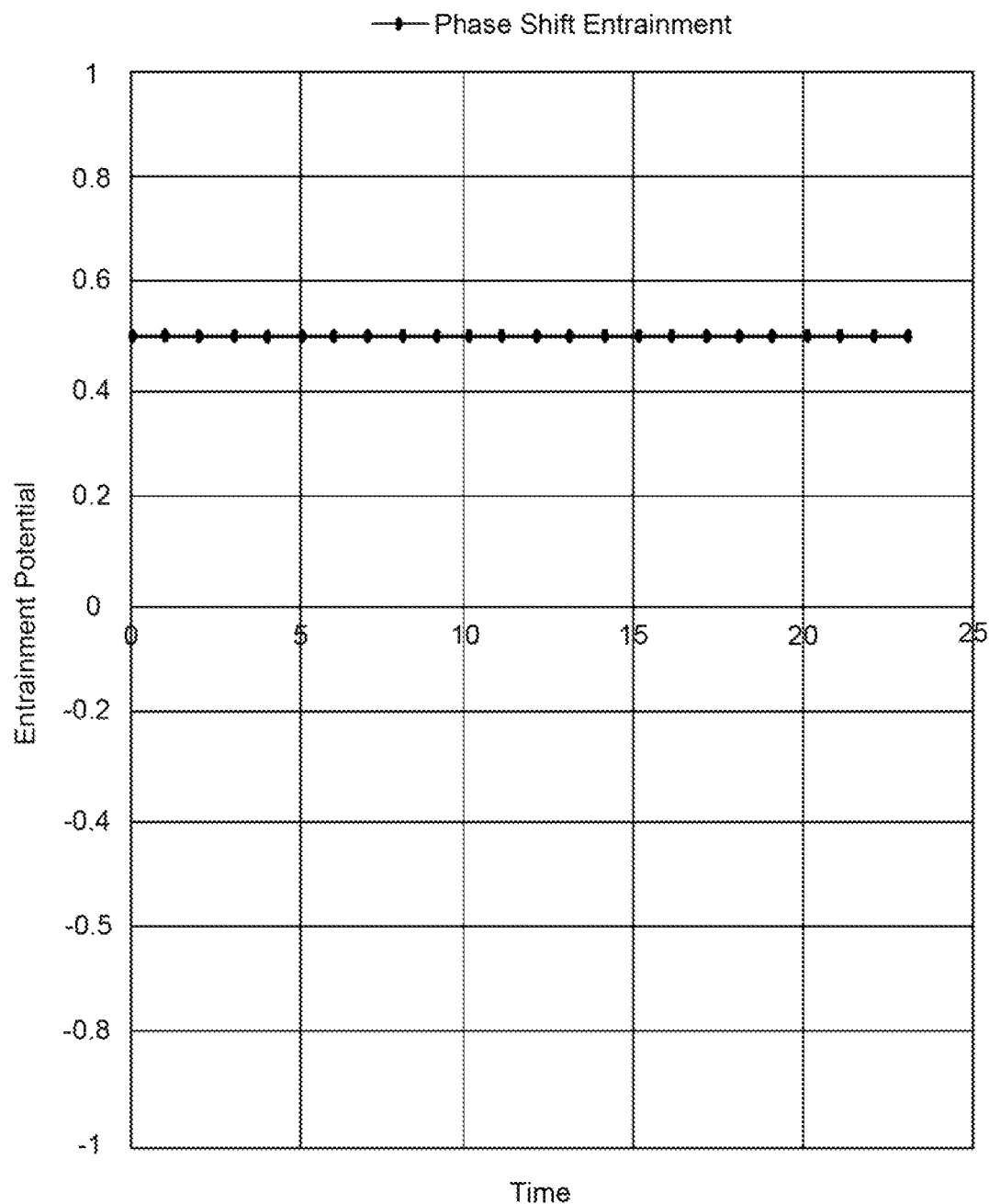

FIGS. 12-13 illustrate examples of entrainment of a patient's gait by use of the system described herein. FIG. 12 illustrates a "perfect" entrainment, e.g., a constant entrainment potential of zero. This occurs when there is no delay, or negligible delay, between the time beat and the associated time step taken in response to the time beat. FIG. 13 illustrates a phase-shift entrainment, e.g., a condition in which the entrainment potential is non-zero, but remains constant, or with minimal variation, over time. This occurs when there is a consistent delay, within tolerances, between the time beat and the time step over time.

With continued reference to FIG. 11, an EP Ratio is calculated as a ratio of the time duration between time beats to the time duration between time steps:

$$EP \text{ Ratio} = \frac{\text{Time Beat 2} - \text{Time Beat 1}}{\text{Time Step 2} - \text{Time Step 1}} \quad [6]$$

Where Time Beat 1 1101 corresponds to the time of a first music beat, and Time Step 1 1102 corresponds to the time of the patient's step in response to Time Beat 1. Time Beat 2 1106 corresponds to the time of a second music beat, and Time Step 2 1108 corresponds to the time of the patient's step in response to Time Beat 2. The goal is for an EP Ratio=1 or EP Ratio/Factor=1. The Factor is determined as follows:

$$2^{round\left(log2\left(\frac{\text{Time Step 2} - \text{TimeStep 1}}{\text{Time Beat 2} - \text{Time Beat 1}}\right)\right)} = \text{Factor} \quad [7]$$

Figure 14:
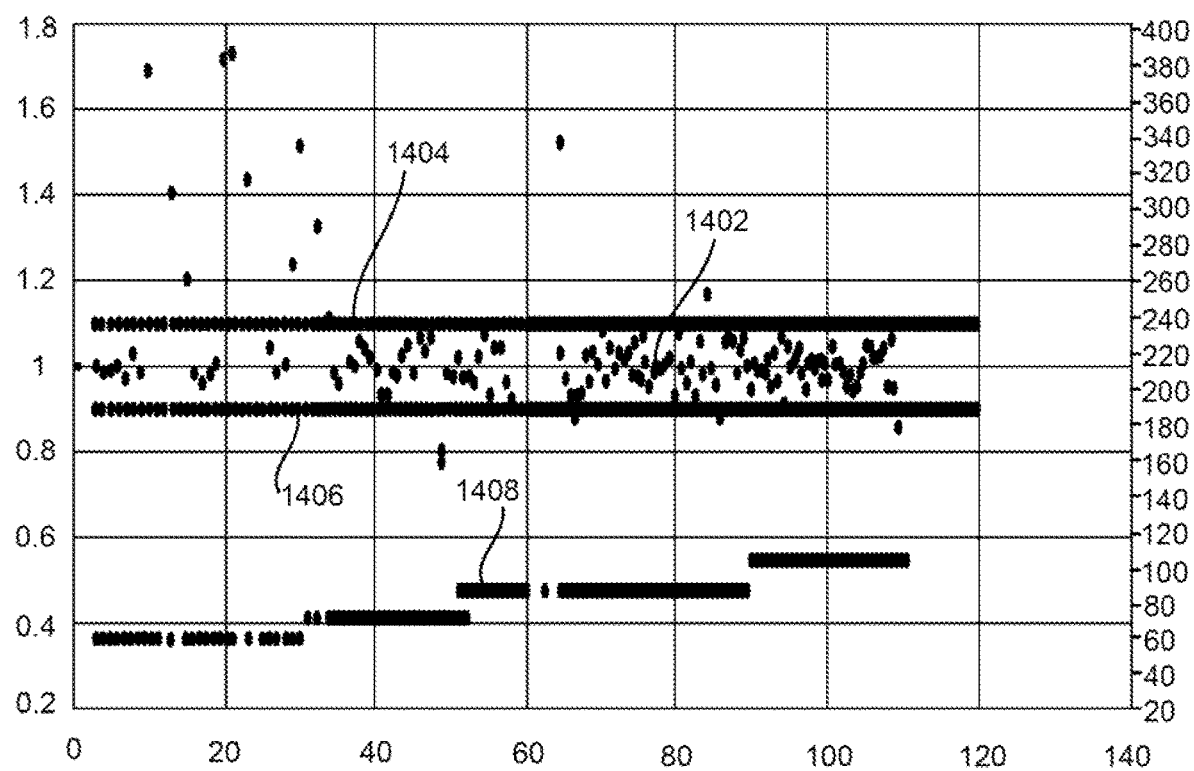
FIGS. 14-15 illustrate a patient response in accordance with exemplary embodiments of the disclosed subject matter.
Figure 15:
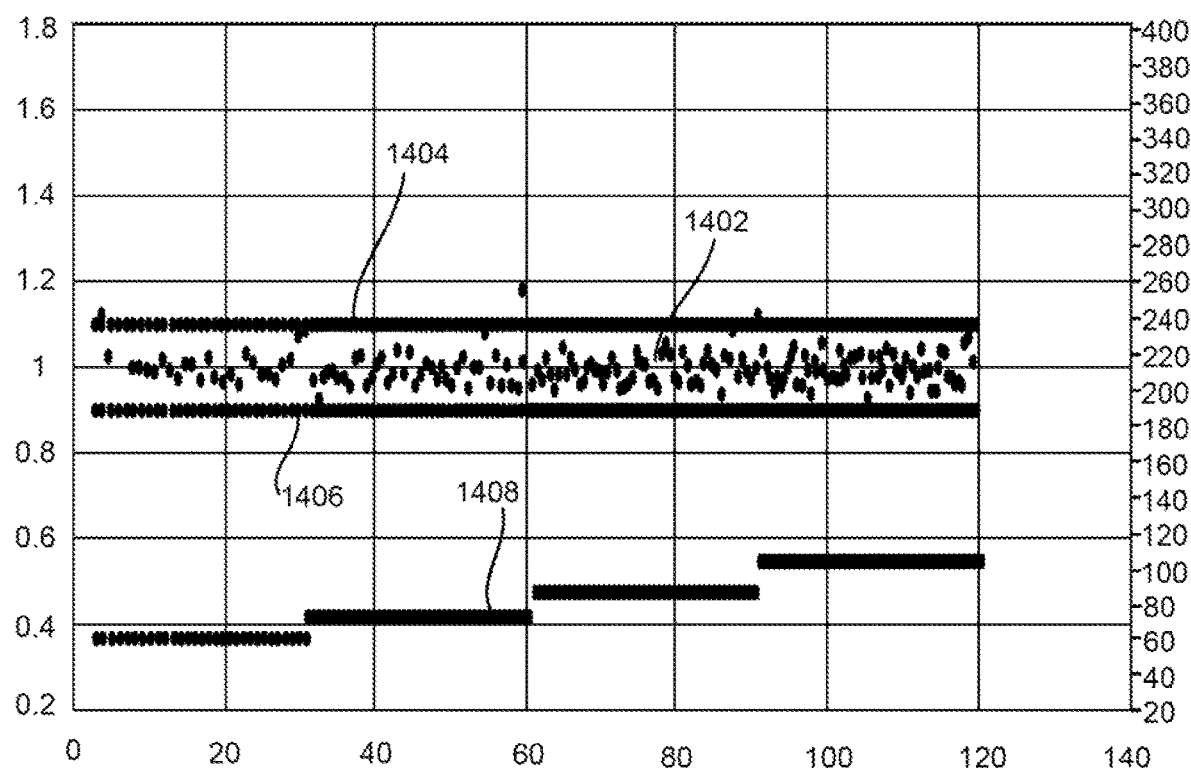

This factor allows the subdivision of beats to happen or for someone to step every 3 beats or 3 out of every 4. It can provide flexibility for different scenarios FIGS. 14 and 15 illustrate the entrainment response over time of a patient using techniques described herein. FIG. 14 (Left Y-axis: EP Ratio; Right Y-axis: Beats Per Minute; X-axis: time) illustrates a scattering of dots 1402 which represent the averages of the EP Ratio of a first patient's gait. The graph illustrates an upper limit 1404 of +0.1 and a lower limit 1406 of −0.1. The lines 1408 illustrate the tempo over time (starting at 60 beats per minute, increasing in steps to 100 bpm). FIG. 14 illustrates that the EP Ratio remains near 1 (±0.1) as the tempo is increased from 60 bpm to 100 bpm. FIG. 15 illustrates the EP ratio of a second patient's gait, in which the EP Ratio also remains near 1 (±0.1) as the tempo is increased from 60 bpm to 100 bpm.

Figure 16:
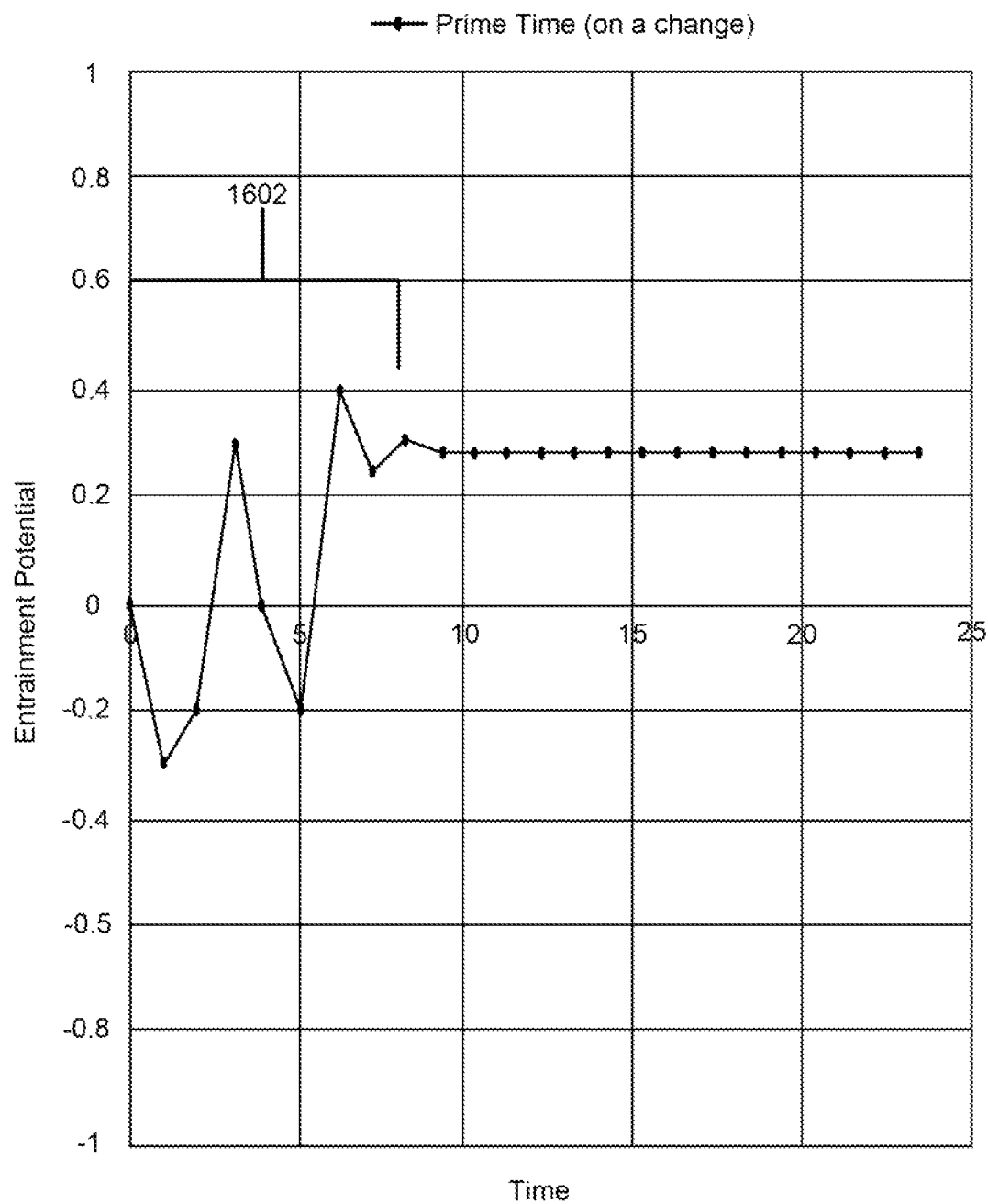
FIGS. 16-17 illustrate a patient response in accordance with exemplary embodiments of the disclosed subject matter.
Figure 17:
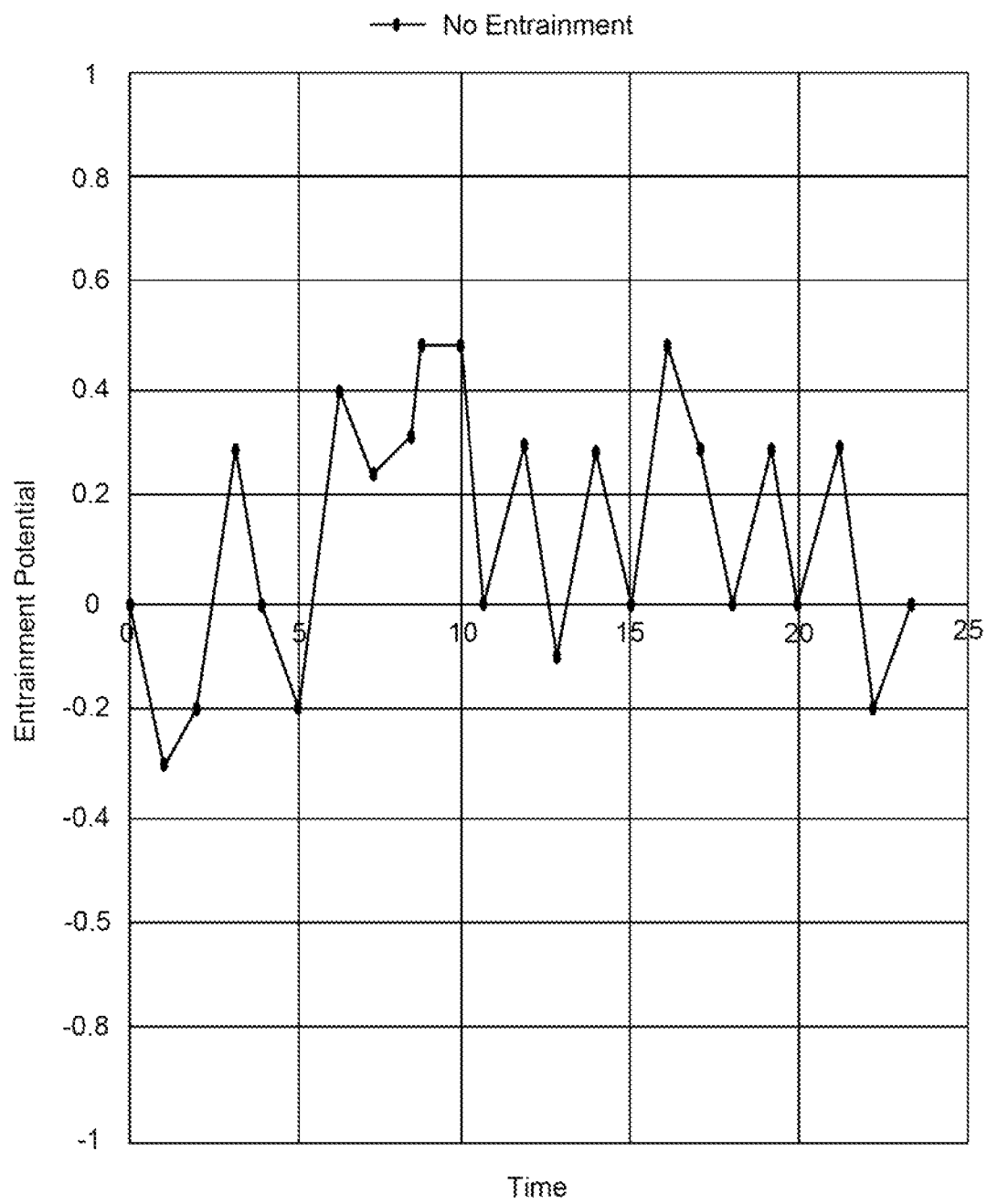

FIGS. 16 and 17 (Y-axis: Entrainment potential, X-axis: Time) illustrate two patients' responses to a change in the time beats (e.g., change in tempo) and/or change to the chords, change in haptic feedback, change in cueing of the feet (e.g., left-right, or left-right-cane cueing), etc. FIG. 16 shows a time based plot in which the patient's gait equilibrates with "perfect entrainment" (constant zero or negligible entrainment potential), or a constant phase-shifted entrainment potential. As illustrated in the figure, it takes a certain period of time, prime time 1602, until equilibration occurs. FIG. 17 illustrates a time-based plot in which the patient's gait does not equilibrate, e.g., does not reach perfect entrainment or a constant phase-shifted entrainment potential after a change to the time beats. Prime time is useful because it represents a set of data that is separate from measuring the accuracy of entrainment. The prime time parameter can also be used to screen future songs for suitability. For example, when patients exhibit a longer prime time value when a music piece is used, such music piece is less capable for therapy.

Figure 18:
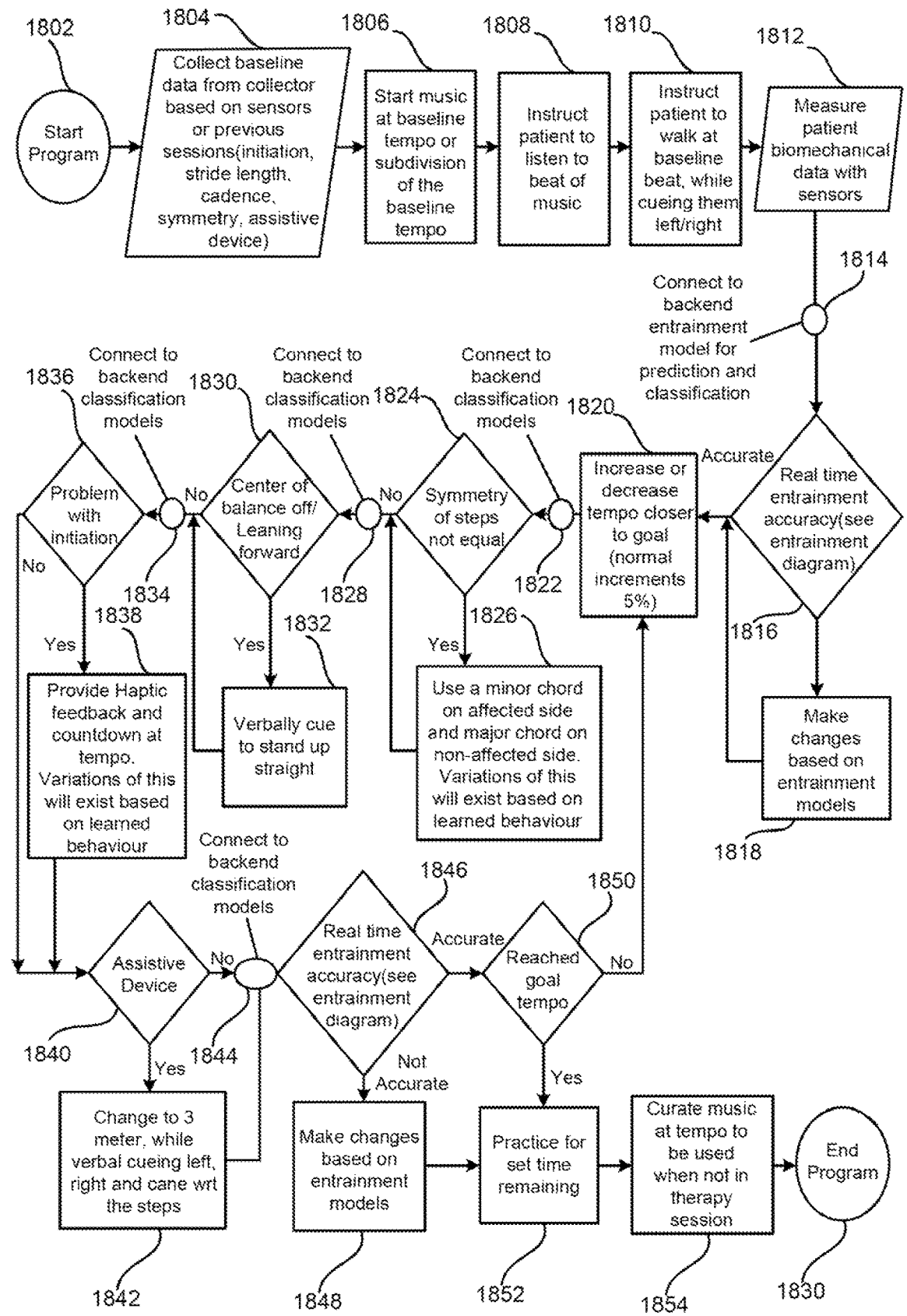
FIG. 18 illustrates an implementation of a technique for gait training of a patient in accordance with exemplary embodiments of the disclosed subject matter.

FIG. 18 illustrates a technique useful for gait training, wherein the repetitive movement refers to the steps taken by the patient while walking. Gait training is adapted to individual patient populations, diagnosis, and conditions to deliver personalized and individualized music interventions. Based on the inputs, the program changes the content, cadence, major/minor chords, meter, and musical cues (e.g., melodic, harmonic, and force cues) where applicable. The program can make selections of music by using date of birth, listed music preferences, and entraining tempo to provide a playlist of passive music to use on a regular basis. The key inputs for gait training are cadence, symmetry and stride length of the user executing the physical activity, e.g., walking. The program uses connected hardware to provide haptic/vibration feedback at the BPM of the music. The appropriate populations for gait training include patients with traumatic brain injury (TBI), stroke, Parkinson's Disease (PD), Multiple Sclerosis (MS), Functional Neurologic Disease (FND), and aging.

The method starts at step 1802. At step 1804, biomechanical data is received at the collector 106 based on data from sensors, e.g., sensors 200, 206, 208. Biomechanical data includes initiation, stride length, cadence, symmetry, data about assistive device, or other such patient feature sets that were stored and generated by the analytics systems 108. Exemplary biomechanical data parameters are listed in Table 1, 2, and 3 above. The baseline condition is determined from a one or more sources of data. First, the patient's gait without any music being played is sensed. Sensor and feature data regarding the patient's initiation, stride length, cadence, symmetry, data about assistive device, etc. comprise the patient's baseline biomechanical data for a therapy session. Second, sensor data from previous sessions of the same patient, as well as any higher level classification data from analytics system 108 comprise the patient's historical data. Third, sensor data and higher level classification data for other similarly-situated patients comprise population data. Thus, the Baseline condition can include data from one or more of (a) the patient's baseline biomechanical data for a therapy session, (b) data from the patient's previous sessions, and (c) population data. The baseline beat tempo is then selected from the baseline condition. For example, a baseline beat tempo can be selected to match the current cadence of the patient prior to playing music. Alternatively, the baseline beat tempo can be selected as a fraction or multiple of the current cadence of the patient. As another alternative, the baseline tempo can be selected to match the baseline beat tempo used in the same patient's previous session. As yet another alternative, the baseline beat tempo can be selected based on baseline beat tempos used for other patients with similar physical conditions. Finally, the baseline beat tempo can be selected based on a combination of any of the data described above. A goal beat tempo can also be determined from this data. For example, the goal beat tempo may be selected as a percentage increase in the baseline beat tempo by reference to the improvement exhibited by other similarly situated patients. The tempo is understood to refer to the frequency of beats in the music.

At step 1806, music provided to the patient on music delivery device 230 (e.g., earbuds or headphones, or a speaker) from handheld device 220 is started at baseline tempo or a subdivision of the baseline tempo. In order to supply music to the patient at the baseline tempo, music is having a constant baseline tempo is selected from a database, or existing music is modified, e.g., selectively sped up or slow down, in order to provide beat signals at a constant tempo.

At step 1808, the patient is instructed to listen to the beat of the music. At step 1810, the patient is instructed to walk at the baseline beat tempo, optionally receiving cues as to left and right feet. The patient is instructed to walk such that each step closely matches the beat of the music, e.g., to walk "in time" with the beat tempo. Steps 1806, 1808, and 1810 may be initiated by the therapist, or by audible or visual instructions on the handheld device 220.

At step 1812, the sensors 200, 206, 208 on the patient are used to record patient data, such as heel strike pressure, 6-Dimensional movement, EMG activity, and a video record of patient movement. All sensor data is time-stamped. Data analysis is performed on the time-stamped sensor data including "gate" analysis discussed herein. For example, analysis of the sensor data, e.g., heel strike pressure, is made in order to determine the onset time of each step. Additional data received includes the time associated with each beat signal of the music provided to the patient.

At step 1814, a connection is made to the entrainment model (e.g., the ensemble machine learning system 410 of the analytics system 108 or models downloaded on collector 106 and running on the handheld device 220) for prediction and classification. (It is understood that such connection may be pre-existing or initiated at this time.) Such connection is typically very fast or instantaneous.

At step 1816, an optional entrainment analysis performed at the analytics systems 108 is applied to the sensor data. The entrainment analysis includes the determination of the delay between the beat signal and the onset of each step taken by the patient. As an output from the entrainment analysis, a determination is made regarding the accuracy of the entrainment, e.g., a measure of the instantaneous relationship between the baseline tempo and the patient's step as discussed above regarding the entrainment potential and EP ratio. If the entrainment is not accurate, e.g., entrainment potential is not constant within a tolerance, adjustments are made at step 1818, e.g., speed up or slow down the beat tempo, increase volume, increase sensory input, overlay metronome or other related sound, etc. If the entrainment is accurate, e.g., entrainment potential is constant within a tolerance, an incremental change is made to the tempo at step 1820. For example, the baseline tempo of the music played with handheld device is increased towards a goal tempo, e.g., by 5%.

At step 1822, a connection is made to the entrainment model for prediction and classification. (It is understood that such connection may be pre-existing or initiated at this time.) At step 1824, an optional symmetry analysis is applied to the sensor data. As an output from the symmetry analysis, a determination is made regarding the symmetry of the patient's gait, e.g., how closely the patient's left foot motion matches the patient's right foot motion for stride length, speed, stance phase, swing phase, etc. If the steps are not symmetrical, e.g., below a threshold, adjustments are made at step 1826 to the music broadcast to the patient by the handheld device. A first modification may be made to the music played during movement of one of the patient's feet, and the second modification may be made to music played during movement of the other one of the patient's feet. For example, a minor chord (or increased volume, sensory input, change in tempo, or overlay of sound/metronome) may be played on one side, e.g., an affected side, and a major chord played on the other side, e.g., a non-affected side. The machine learning system 410 predict in advance when symmetry problems are coming based on the 'fingerprint' of the scenarios leading up to it, e.g., by analyzing motions that are indicative of asymmetry. Asymmetry can be determined by comparing the normal gait parameters for someone with their background can determine how affected the side is and compared to other side.

At step 1828, connection is made to the entrainment model for prediction and classification. (It is understood that such connection may be pre-existing or initiated at this time.) At step 1830, an optional center of balance analysis, e.g., whether the patient is leaning forward, is performed on the sensor data. The analysis may be performed by combining outputs of the foot sensors, as well as the video output. As an output from the center of balance analysis, a determination is made regarding whether the patient is leaning forward. If the patient is leaning forward, a cue to the patient to "stand up straight" is made at step 1832, provided by the therapist, or by audible or visual instructions on the handheld device.

At step 1834, a connection is made to the entrainment model for prediction and classification. (It is understood that such connection may be pre-existing or initiated at this time.) At step 1836, an initiation analysis is applied to the sensor data, e.g., patient's exhibits hesitation or difficulty initiating walking. As an output from the initiation analysis, a determination is made regarding the whether the patient exhibits a problem with initiation. If the patient exhibits a problem with initiation, e.g., below a threshold, haptic feedback can be provided to the patient, which may include a countdown at the beat tempo or a countdown prior to the beginning of a song at step 1838.

At step 1840, it is optionally determined whether the patient is using an assistive device, e.g., a cane, crutches, walker, etc. In some embodiments, the handheld device 220 provides a user interface for the patient or therapist to enter information regarding the use of an assistive device. If a cane is present, the analysis is changed to three meter, e.g., cane, right foot, left foot, and cueing by "left foot," "right foot," and "cane," is made at step 1842, provided by the therapist, or by audible or visual instructions on the handheld device.

At step 1844, a connection is made to the entrainment model for prediction and classification. (It is understood that such connection may be pre-existing or initiated at this time.) An optional entrainment analysis 1846 is applied to the sensor data, substantially as described above in step 1816, with the differences noted herein. For example, entrainment may be compared with previous entrainment data from earlier in the session, from previous sessions with the patient, or with data relating to entrainment of other patients. As an output from the entrainment analysis, a determination is made regarding the accuracy of the entrainment, e.g., how closely the patient's gait matches the baseline tempo. If the entrainment is not accurate, adjustments are made at step 1848, substantially in the same manner as described above at step 1818.

If the entrainment is accurate, a determination is made at step 1850 whether the patient is walking at the goal tempo. If the goal tempo is not reached, the method proceeds to step 1820 (described above), so that an incremental change is made to the tempo. For example, the baseline tempo of the music played with handheld device is increased or decreased, e.g., by 5%, towards the goal tempo. If the goal tempo has been reached, the patient may continue the therapy for the remaining time in the session (step 1852). At step 1854, music at the desired tempo to be used when not in therapy session can be curated and left on the device 220 in FIG. 2. This music content is used as homework/practice by the patient between dedicated therapy sessions. At step 827, the program ends.

Is understood that the steps described above and illustrated in FIG. 18 may be performed in a different order than that disclosed. For example, the evaluations at steps 1816, 1824, 1830, 1836, 1840, 1846, and 1850 may be performed at the same time. Moreover, the plurality of connections to the analytics system 108 (e.g., steps 1814, 1822, 1828, 1834, and 1844) may be performed once throughout the therapy session described.

Figure 19:
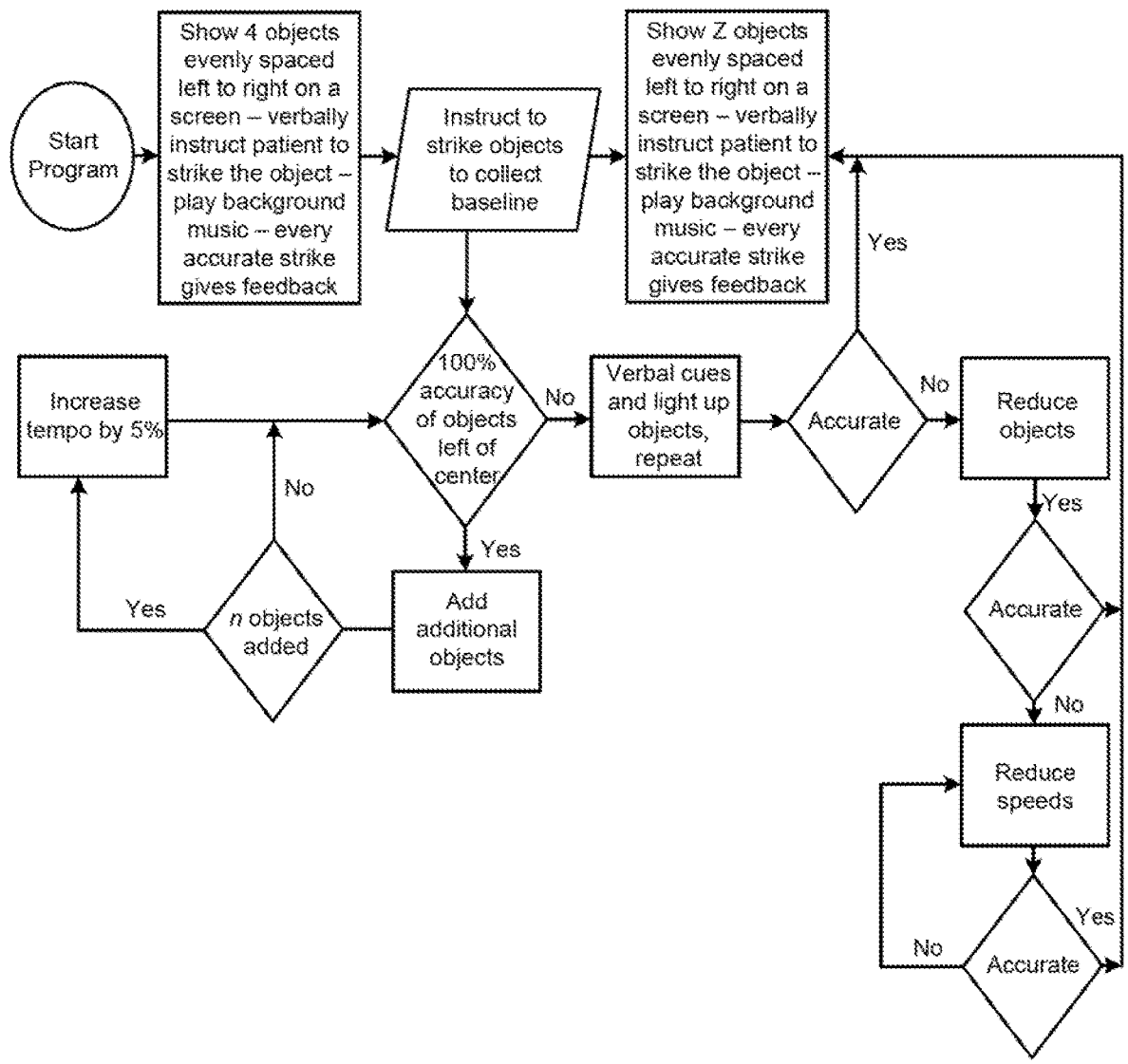
FIG. 19 illustrates an implementation of a technique for neglect training of a patient in accordance with exemplary embodiments of the disclosed subject matter.

FIG. 19 illustrates a technique useful for neglect training. For neglect training, the system and methods described herein use connected hardware to provide haptic/vibration feedback as the patients correctly hit the target. The connected hardware includes a device, video motion capture system or connected bell. All of these devices connect into the system described, vibrate as tapped, and have a speaker to play auditory feedback. For example, the connected bell provides data to the system in the same manner as the sensors 200, e.g., data regarding the bell strike by the patient. The video motion capture system provides video data to the system in the same manner as the video cameras 206. The key inputs for neglect training are information relating to the tracking of movement to a specific location. The program uses connected hardware to provide haptic/vibration feedback as the patient correctly hits the target. The appropriate populations for neglect training include patients with spatial neglect or unilateral visual neglect conditions.

Figure 20:
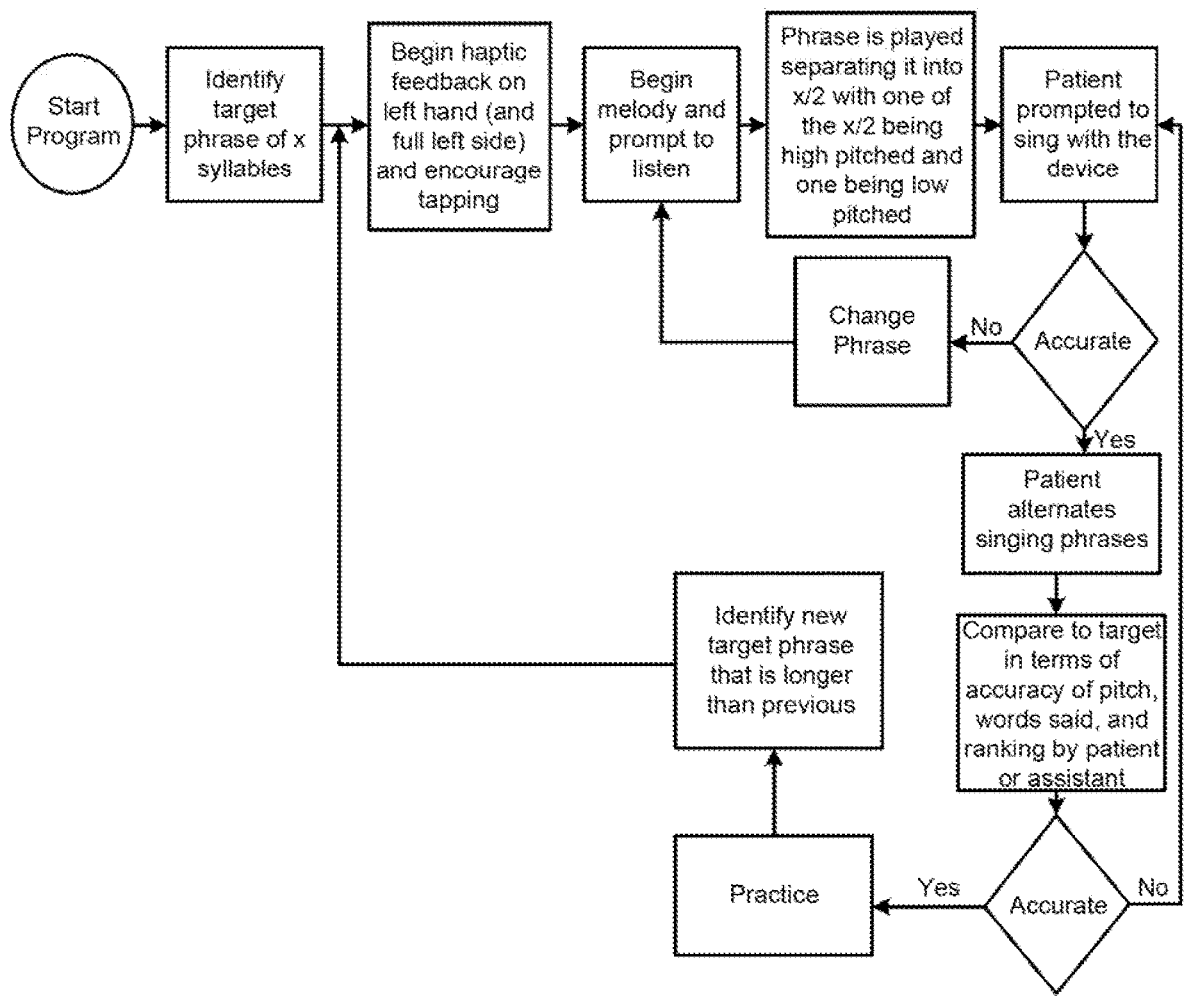
FIG. 20 illustrates an implementation of a technique for intonation training of a patient in accordance with exemplary embodiments of the disclosed subject matter.

The flow diagram illustrated in FIG. 19 for neglect training is substantially identical to the flow illustrated in FIG. 18 for gait training, with the differences noted herein. For example, a baseline test establishes the status of the patient and/or improvement from previous tests. In some embodiments the baseline tests include showing four objects evenly spaced left to right on a screen, e.g., display 222 of handheld device 220. The patient is instructed, either by cues appearing on the display 222 or verbally by a therapist, to strike the object in time with the beats of the background music. As with gait training, the patient is instructed to strike a bell in time with the beat of the background music. Every accurate strike provides feedback. Once the baseline information is collected, a number of objects evenly spaced left to right are displayed on a screen. As above, the patient is instructed to strike the objects in order from left to right in time with the beats of the background music. Every accurate strike provides a feedback. As with gait training, the analytics system 108 evaluates the patient's responses and classifies the responses and provide instructions to add or reduce objects, or increase or decrease tempo of the music to reach a goal tempo FIG. 20 illustrates a technique useful for intonation training. For intonation training, the system and methods described herein relies on voice processing algorithms. The phrases typically chosen are common words in the following categories: bilabials, gutturals, and vowels. The hardware is connected to a patient to provide haptic feedback at the beats per minute to one hand of the patient. The key inputs for intonation training are the tone of voice and words spoken and rhythm of speech. The appropriate populations for intonation training include patients with Broca's aphasia, expressive aphasia, non-fluent aphasia, apraxia, autism spectrum disorder, and Down's syndrome.

The flow diagram illustrated in FIG. 20 for intonation training is substantially identical to the flow illustrated in FIG. 18 for gait training, with the differences noted herein. For example, haptic feedback is provided to one hand of the patient to encourage tapping. The patient is then instructed, either by cues appearing on the display 222 or verbally by a therapist, to listen to the music played. The spoken phrase to be learned is played by separating it into two parts, with the first one of the two parts being high-pitched and the second of the two parts being low pitched. The patient is then instructed, either by cues appearing on the display 222 or verbally by a therapist, to singing the phrase with the device using the two pitches being played. As with gait training, the analytics system 108 evaluates the patient's responses and classifies the responses in terms of accuracy of pitch, words spoken, and ranking by patient or assistant/therapist, and provide instructions to provide alternate phrases and compare responses to targeted speech parameters.

Figure 21:
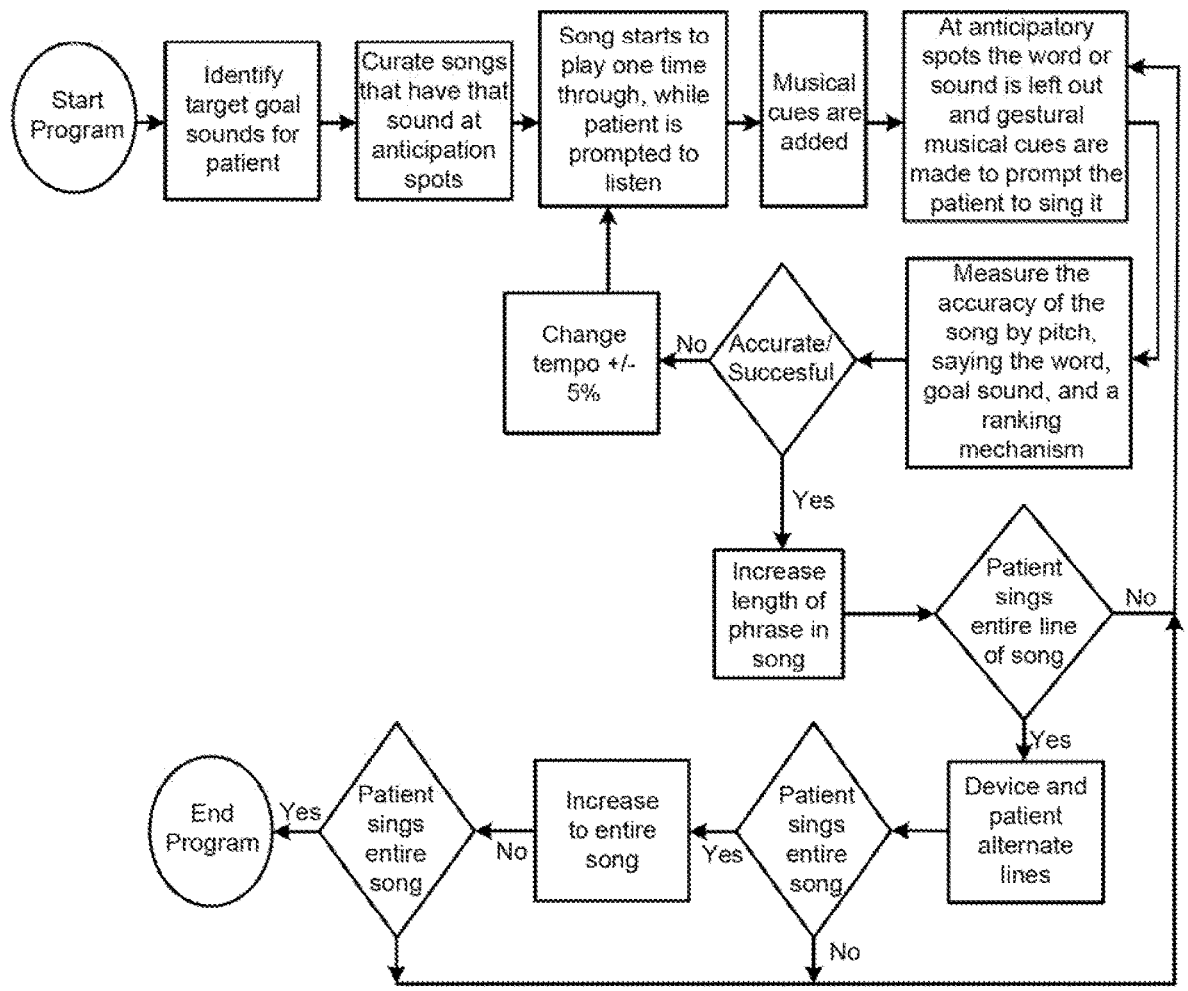
FIG. 21 illustrates an implementation of a technique for musical stimulation training of a patient in accordance with exemplary embodiments of the disclosed subject matter.

FIG. 21 illustrates a technique useful for musical stimulation training. For musical stimulation training, the system and methods described herein relies on voice processing algorithms. Familiar songs are used with an algorithm to separate the anticipatory section out (referred to as an expectancy violation). The hardware includes a speaker for receiving and processing the singing by the patient, and in some embodiments a therapist can manually provide an input regarding singing accuracy. Key inputs are information relating to the tone of voice and words spoken and rhythm of speech, and music preferences. The appropriate populations include patients with Broca's aphasia, non-fluent aphasia, TBI, stroke, and primary progressive aphasia.

The flow diagram illustrated in FIG. 21 for musical stimulation training is substantially identical to the flow illustrated in FIG. 18 for gait training, with the differences noted herein. For example, a song is played for the patient, and the patient instructed either by cues appearing on the display 222 or verbally by a therapist, to listen to the song. Musical cues are added to the song. Subsequently, at anticipatory spots, a word or sound is left out and gestural music cues are played to prompt the patient to sing the missing word or sound. As with gait training, the analytics system 108 evaluates the patient's responses and classifies the responses in terms of accuracy of pitch, words spoken, and ranking by patient or assistant/therapist, and provide instructions to play additional portions of the song in order to improve speech to targeted speech parameters.

Figure 22:
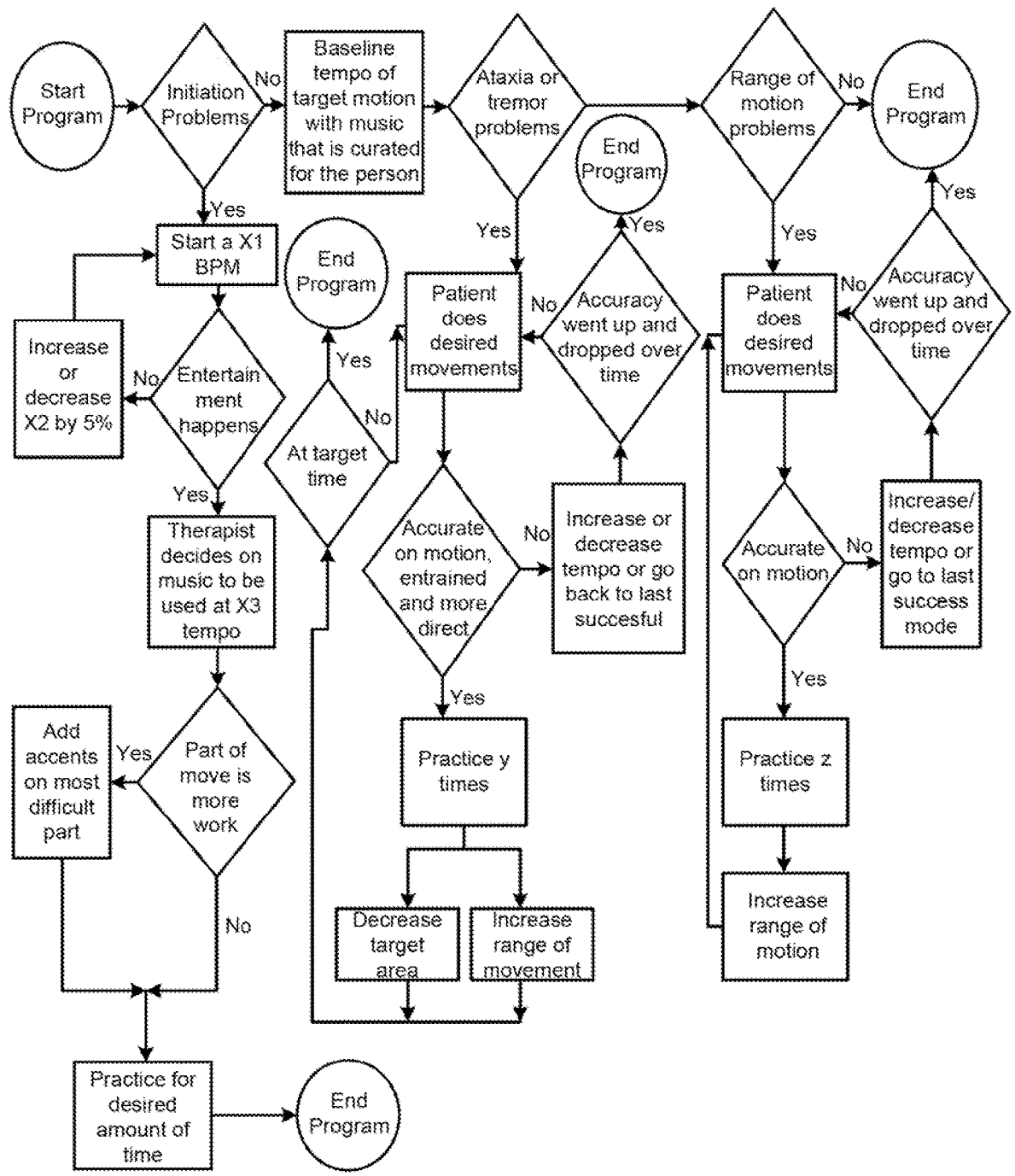
FIG. 22 illustrates an implementation of a technique for gross motor training of a patient in accordance with exemplary embodiments of the disclosed subject matter.

FIG. 22 illustrates a technique useful for gross motor training. For gross motor training, the system and methods described herein are directed to help with ataxia, range of motion or initiation. The more challenging portion of an exercise is musically "accented", e.g., by the use of melodic, harmonic, rhythmic, and/or force cues. Key inputs are information relating to movements in X, Y, and Z-capture via connected hardware or video camera system. The appropriate populations include patients with neurological, orthopedic, strength, endurance, balance, posture, range of motion, TBI, SCI, stroke, and Cerebral Palsy.

The flow diagram illustrated in FIG. 22 for gross motor training is substantially identical to the flow illustrated in FIG. 18 for gait training, with the differences noted herein. As with gait training, the patient's is provided with cues to move in time with the baseline beats of a musical selection. The analytics system 108 evaluates the patient's responses and classifies the responses in terms of accuracy of motion and entrainment as discussed above and provides instructions to increase or decrease the tempo of the music played.

Figure 23:
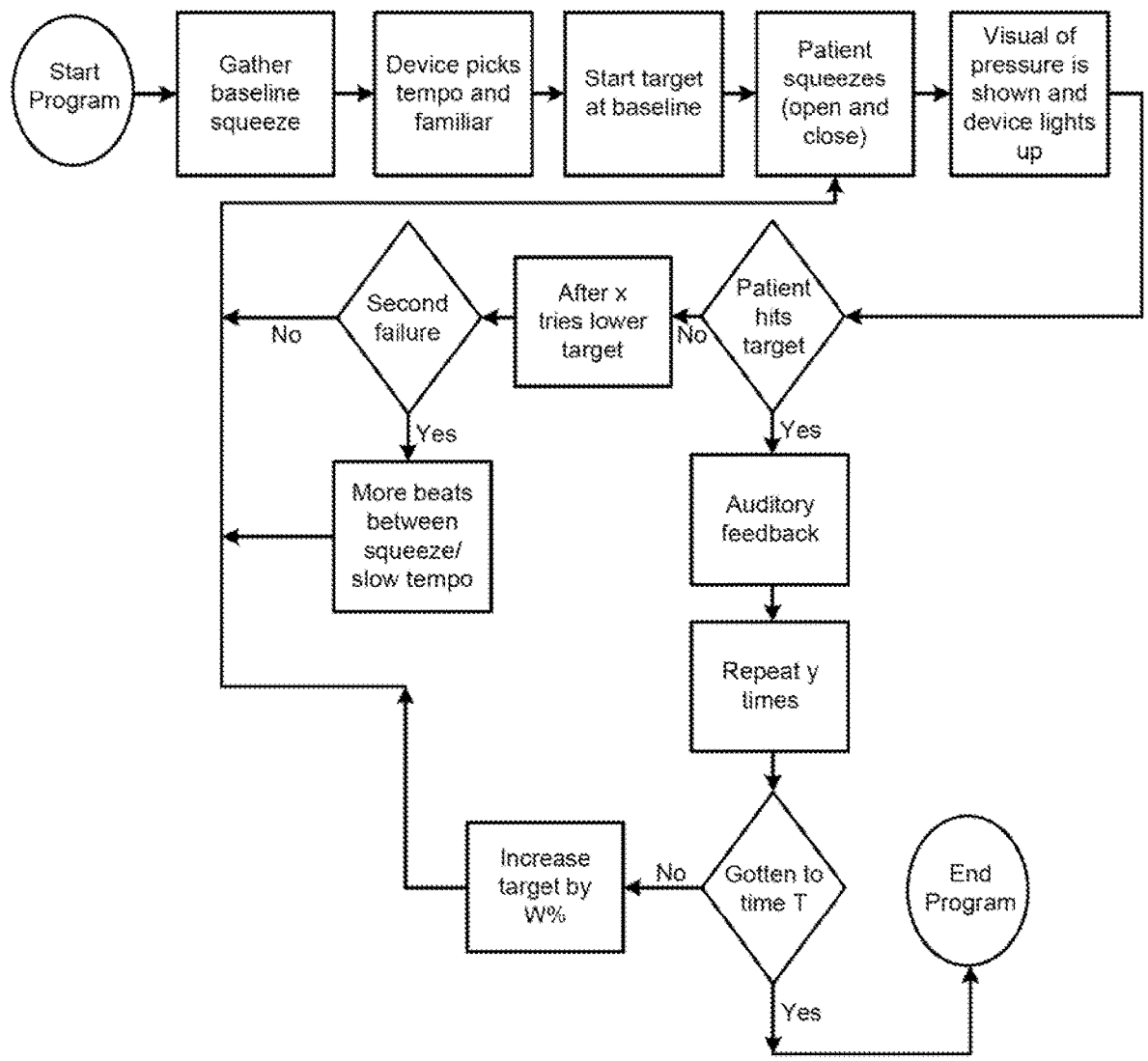
FIG. 23 illustrates an implementation of a technique for grip strength training of a patient in accordance with exemplary embodiments of the disclosed subject matter.

FIG. 23 illustrates a technique useful for grip strength training. For grip strength training, the system and methods described herein rely on sensors associated with the gripper device. The hardware includes a gripper device having pressure sensors, a connected speaker associated with a handheld device 220. Key inputs are the pressure provided by the patient to the gripping device in a similar manner to the heel strike pressure measured by sensor 200. The appropriate populations include patients with neurological, orthopedic, strength, endurance, balance, posture, range of motion, TBI, SCI, stroke, and Cerebral Palsy.

The flow diagram illustrated in FIG. 23, for grip strength training is substantially identical to the flow illustrated in FIG. 18 for gait training, with the differences noted herein. As with gait training, the patient is provided with cues to apply force to the gripping device in time with the baseline beats of a musical selection. The analytics system 108 evaluates the patient's responses and classifies the responses in terms of accuracy of motion and entrainment as discussed above and provides instructions to increase or decrease the tempo of the music played.

Figure 24:
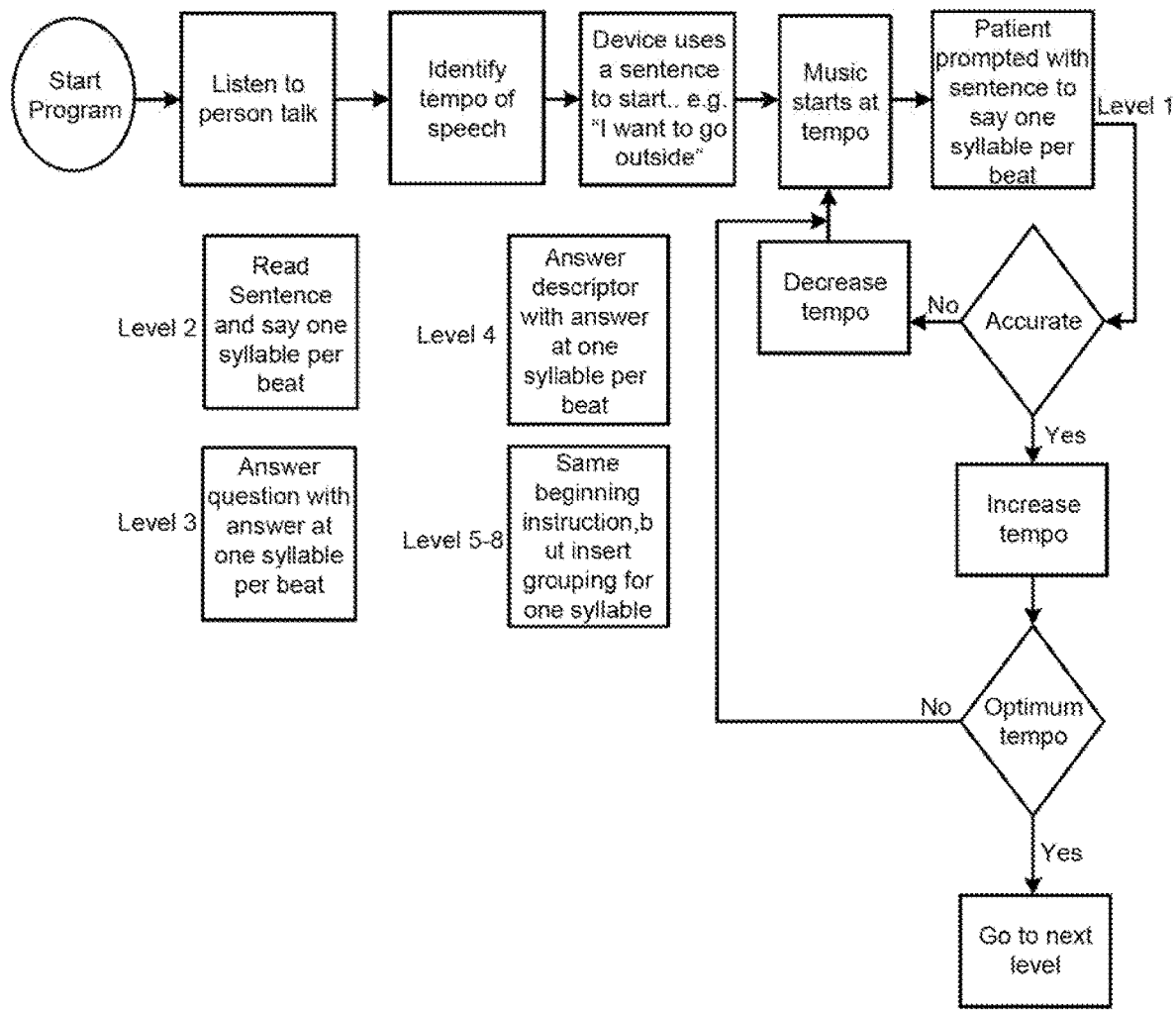
FIG. 24 illustrates an implementation of a technique for speech cueing training of a patient in accordance with exemplary embodiments of the disclosed subject matter.

FIG. 24 illustrates a technique useful for speech cueing training. For speech cueing training, the system and methods described herein relies on voice processing algorithms. The hardware can include a speaker for receiving and processing the singing by the patient, and in some embodiments a therapist can manually provide an input regarding speech accuracy. Key inputs are the tone of voice and words spoken and rhythm of speech, and music preferences. The appropriate populations include patients with robot, word finding and stuttering speech issues.

The flow diagram illustrated in FIG. 24 for speech cueing training is substantially identical to the flow illustrated in FIG. 18 for gait training, with the differences noted herein. As with gait training, the patient is provided with cues to speak a sentence, either by cues appearing on the display 222 or verbally by a therapist, by saying one syllable in time with each beat of a musical selection. The analytics system 108 evaluates the patient's speech and classifies the responses in terms of accuracy of speech and entrainment as discussed above and provides instructions to increase or decrease the tempo of the music played.

Figure 25:
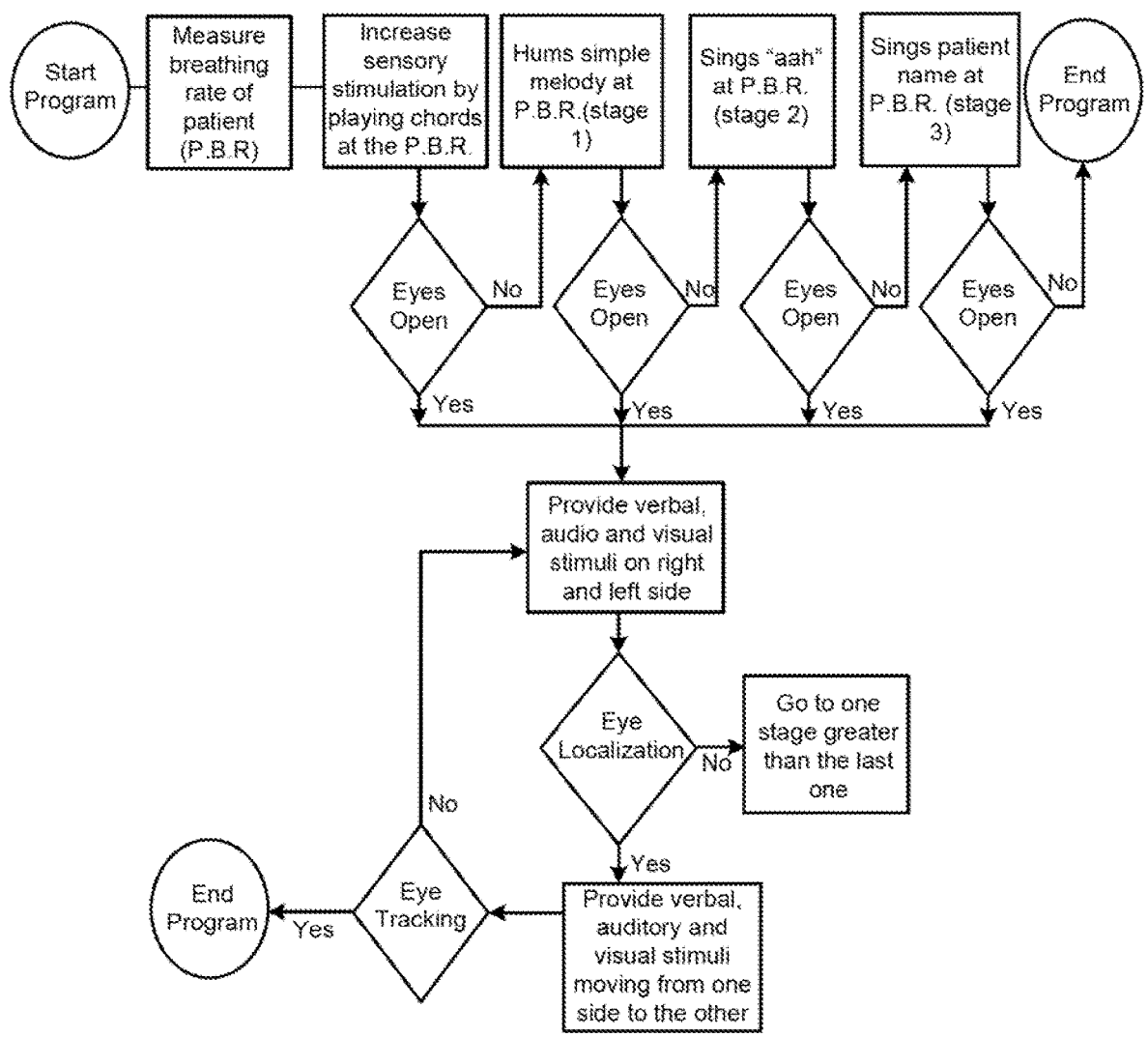
FIG. 25 illustrates an implementation of a technique for training of a minimally conscious patient in accordance with exemplary embodiments of the disclosed subject matter.

FIG. 25 illustrates a technique useful for training of minimally conscious patients. The system and methods described herein rely on an imaging system, such as a 3-D camera, to measure if the eyes of the patient are open, the direction the patient is looking, and the resulting patient pulse or heart rate. The program searches and optimizes for the heart rate, stimulation, respiration rate, eye closure, posturing, and restlessness. The appropriate populations include patients with coma and disorders of consciousness.

The flow diagram illustrated in FIG. 25 for training of minimally conscious patients is substantially identical to the flow illustrated in FIG. 18 for gait training, with the differences noted herein. As with gait training, the patient is provided with increasing stimulation at the breathing rate of the patient (PBR). For example, the patient is first provided with stimulation at the PBR of musical chords and observing whether the patient's eyes are open. If the patient's eyes are not open, the stimulation sequentially increases from humming a simple melody at PBR, to singing "aah" at the PBR, to singing the patient's name at the PBR (or playing a recording of such sounds), and checking at each input whether the patient's eyes are open. The analytics system 108 evaluates the patient's eye tracking and classifies the responses in terms of level of consciousness and provides instructions to change the stimulation.

Figure 26:
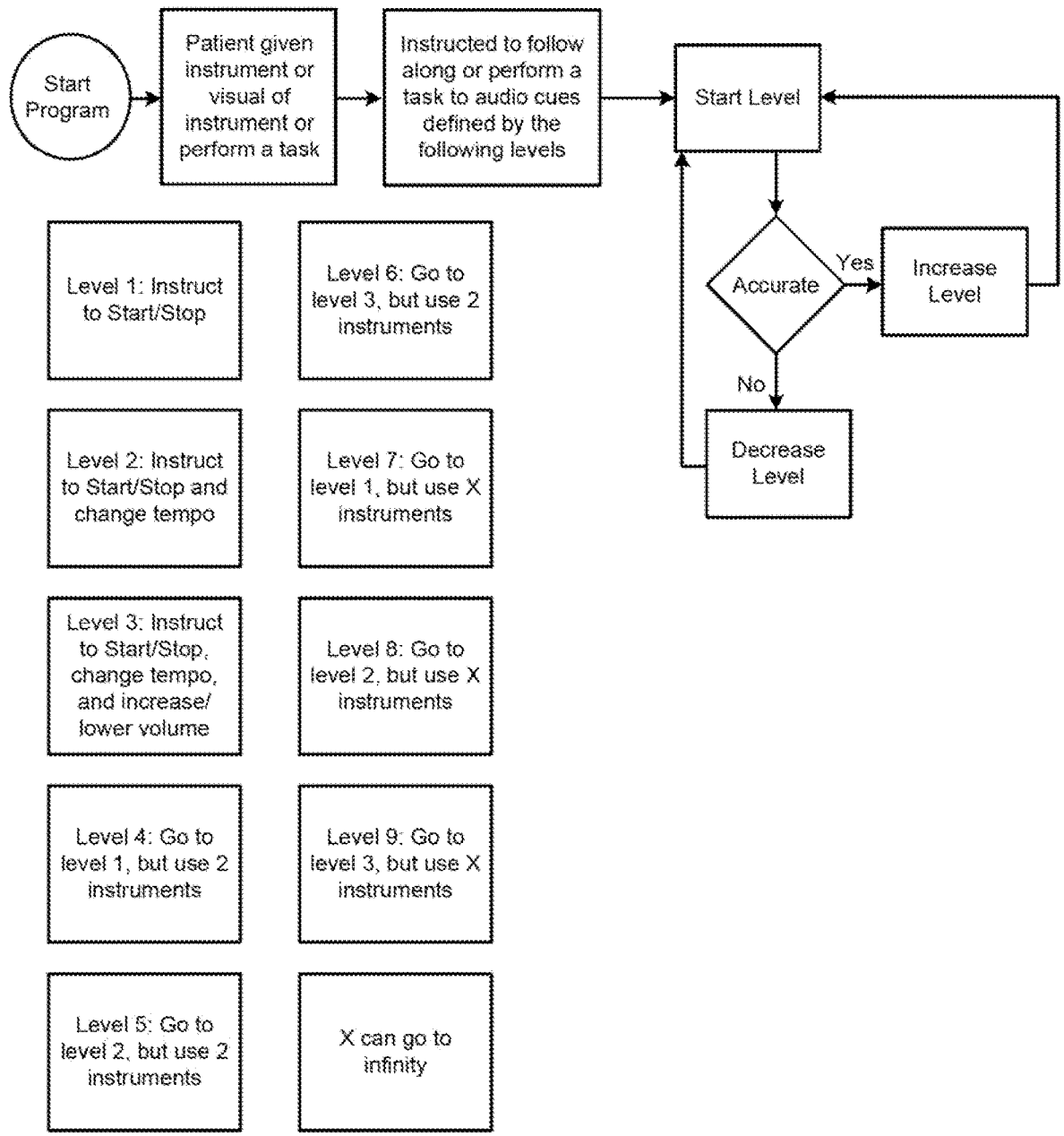
FIGS. 26-28 illustrates an implementation of a technique for attention training of a patient in accordance with exemplary embodiments of the disclosed subject matter.
Figure 27:
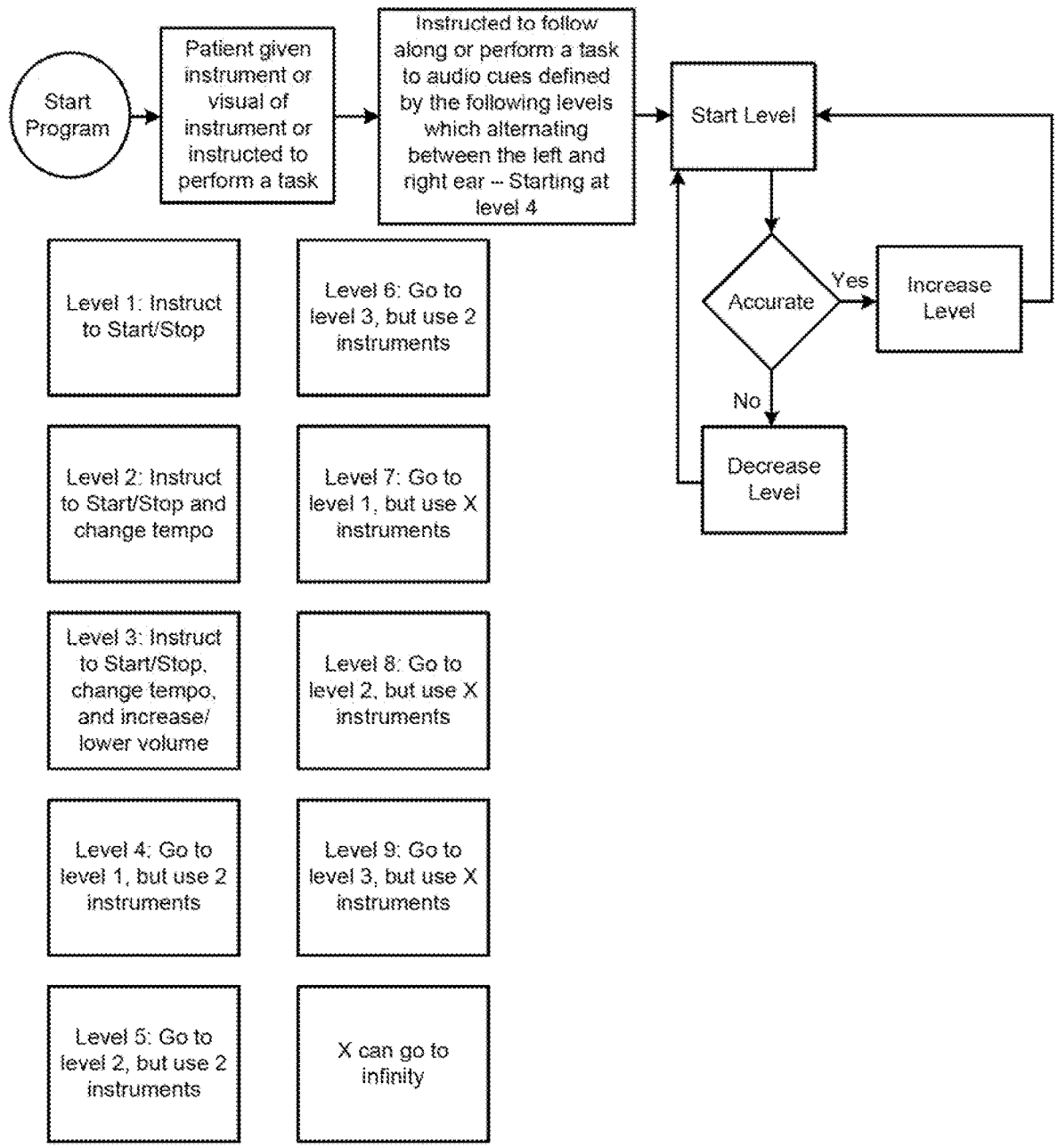
Figure 28:
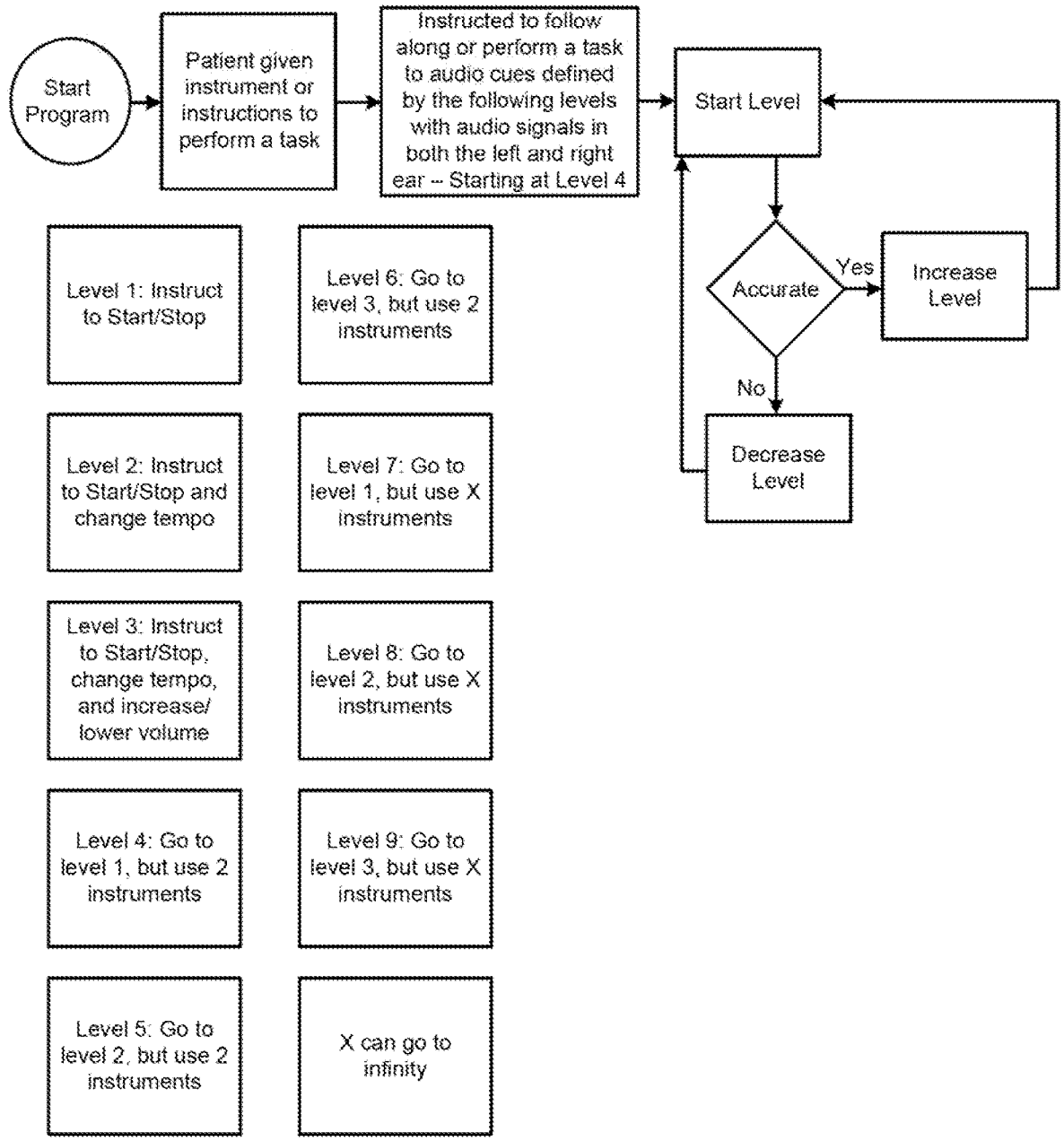

FIGS. 26-28 illustrate a technique useful for attention training. For attention training, the system and methods described herein operate in a closed loop fashion to help patients sustain, divide, alternate and select attention. No visual cue is allowed to signal which movements to make. The appropriate populations include patients with brain tumor, multiple sclerosis, Parkinson's disease, and neurological disease and injury.

The flow diagram illustrated in FIG. 26 for sustained attention training is substantially identical to the flow illustrated in FIG. 18 for gait training, with the differences noted herein. As with gait training, the patient is provided with an instrument (e.g., any instrument could work, such as a drumstick, drum, keyboard, or wirelessly connected version of each) and is instructed, either by cues appearing on the display 222 or verbally by a therapist, to follow along or perform a task to audio cues defined by levels 1 through 9 as illustrated in FIG. 26. The analytics system 108 evaluates the patient's ability to accurately complete the task and classifies the responses to change the tempo or the difficulty of the task. Similarly, FIG. 27 illustrates a flow diagram for alternating attention training in which the instructions are provided, either by cues appearing on the display 222 or verbally by a therapist, to follow along or perform a task to audio cues which alternate between the left and the right ear. FIG. 28 illustrates a flow diagram for divided attention in which the instructions are provided to follow along or perform a task to audio cues with audio signals in both the left and right ear.

Figure 29:
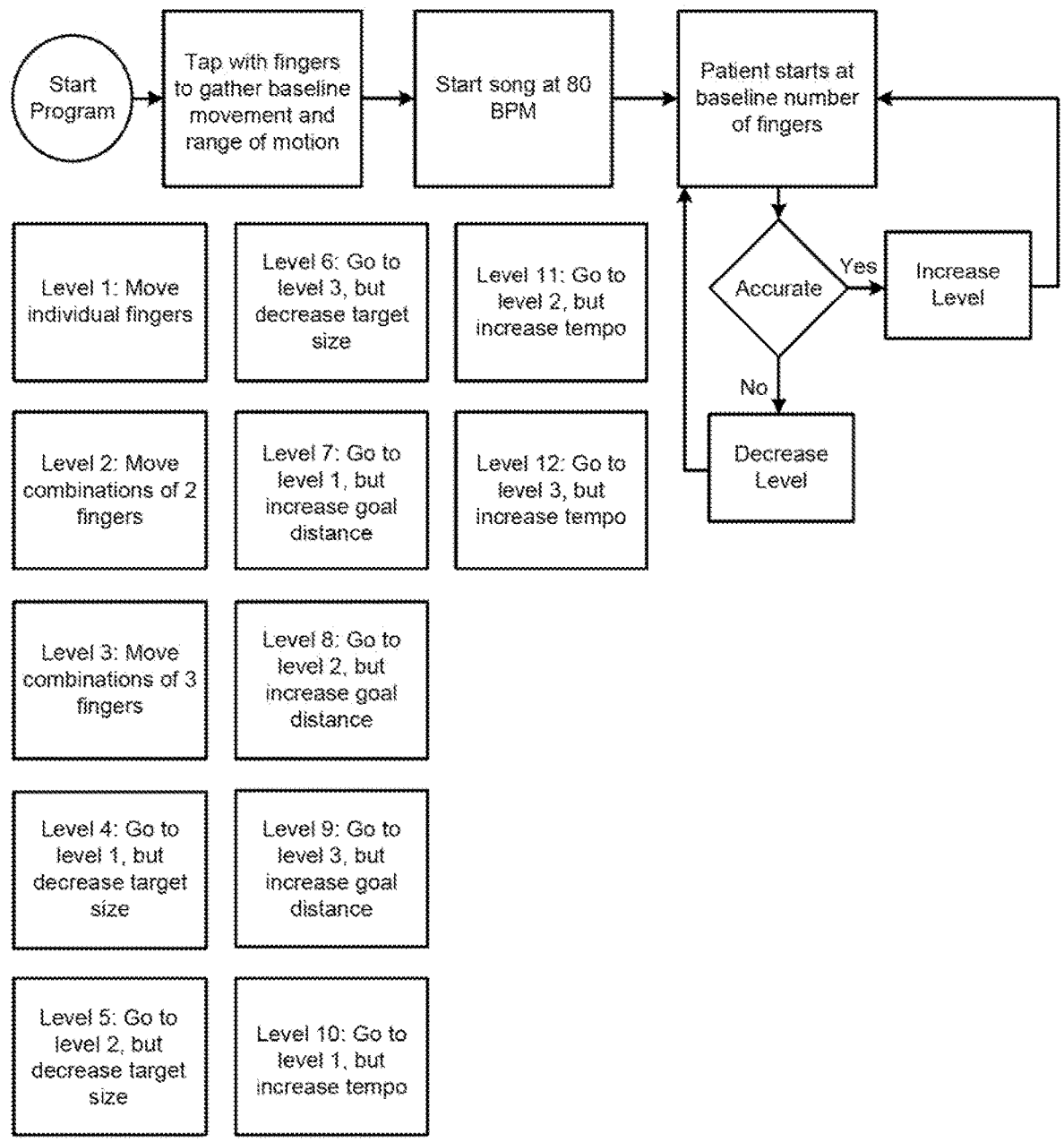
FIG. 29 illustrates an implementation of a technique for dexterity training of a patient in accordance with exemplary embodiments of the disclosed subject matter.

The flow diagram illustrated in FIG. 29 for dexterity training is substantially identical to the flow illustrated in FIG. 18 for gait training, with the differences noted herein. For dexterity training, the patient is instructed to tap with their fingers on the keyboard of the piano to gather baseline movement and range of motion information. The song is started at a particular beat per minute, and the patient starts tapping with the baseline number of fingers. The analytics system 108 evaluates the patient's ability to accurately complete the task and classifies the responses to change the tempo or the difficulty of the task.

Figure 30:
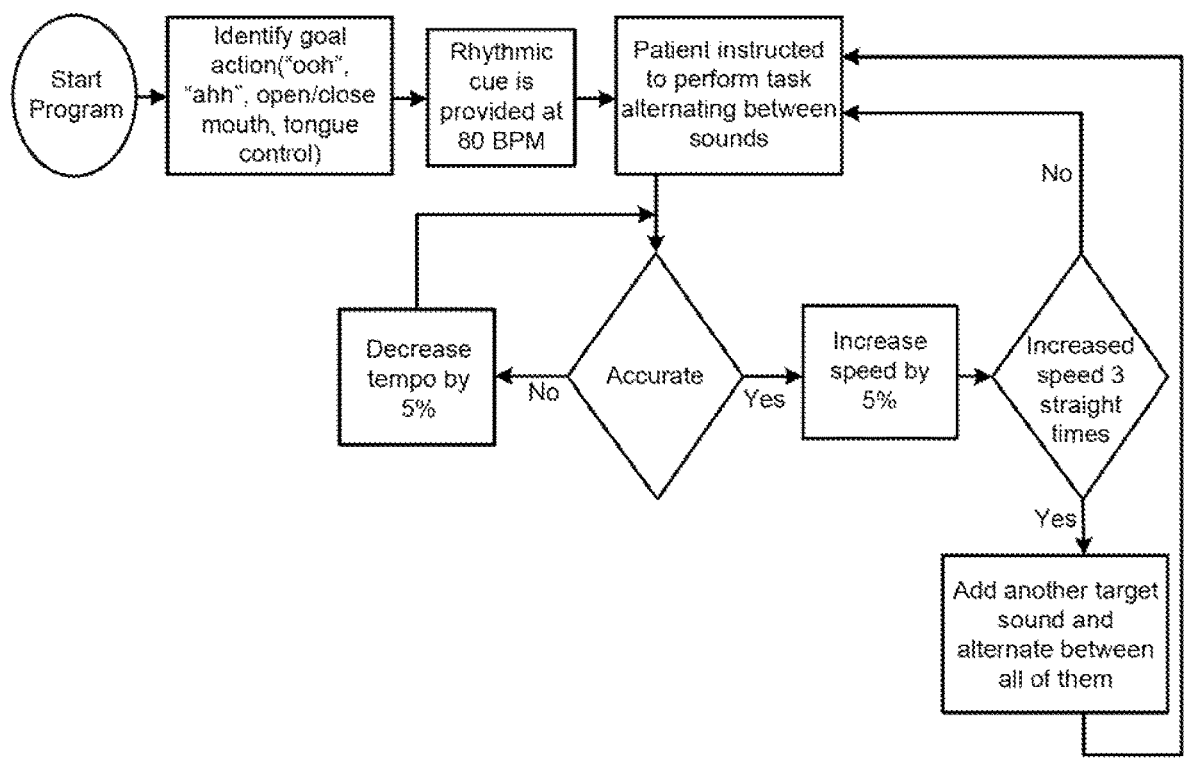
FIG. 30 illustrates an implementation of a technique for oral motor training of a patient in accordance with exemplary embodiments of the disclosed subject matter.

The flow diagram illustrated in FIG. 30 for oral motor training is substantially identical to the flow illustrated in FIG. 18 for gait training, with the differences noted herein. For oral motor training, the patient is instructed to perform a task alternating between two sounds, e.g., "ooh" and "aah." The analytics system 108 evaluates the patient's ability to accurately complete the task and classifies the responses to change the tempo or the difficulty of the task, e.g., by providing a different target sound.

Figure 31:
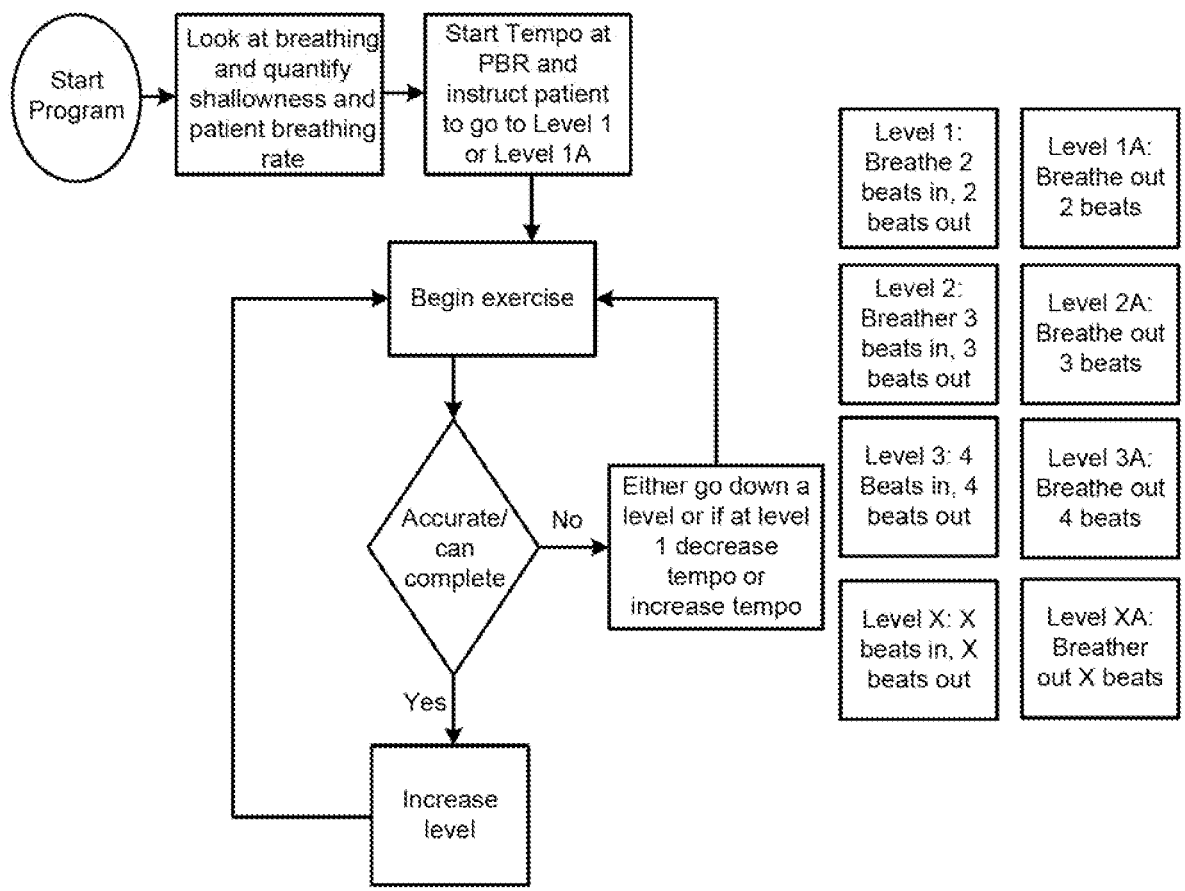
FIG. 31 illustrates an implementation of a technique for respiratory training of a patient in accordance with exemplary embodiments of the disclosed subject matter.

The flow diagram illustrated in FIG. 31 for respiratory training is substantially identical to the flow illustrated in FIG. 18 for gait training, with the differences noted herein. For respiratory training, a baseline breathing rate and shallowness of breathing is determined. Music is provided with a baseline tempo at the patient's breathing rate, and the patient is instructed to perform breathing tasks has described in the levels in FIG. 31. The analytics system 108 evaluates the patient's ability to accurately complete the task and classifies the responses to change the tempo or the difficulty of the task, e.g., by providing a different breathing pattern.

According to a further aspect of the disclosed embodiments, described herein are a method, system and apparatus for determining the optimal biomechanical signals—including, but not limited to motion signals—to support next generation Medical/Therapy systems as it relates to the improvement or maintenance of motor function. This includes a method for calculating gait specific parameters for patients with walking deficiencies caused by neurologic injury or disease or any brain-related decline. This invention also includes the ability to fuse the biometric signals, the patient, and audio content into a synchronized state taking advantage of the ability of direct stimulation, such as Rhythmic Auditory Stimulus (RAS) and Auditory Motor Entrainment (AME) to improve motor function.

As discussed in connection with the exemplary gait-training systems and techniques above (see e.g., FIG. 18), the exemplary processes implemented by the music therapy center 110 for determining if a person is entrained while walking involves calculating how close a person's steps are compared to the beat or beat pulses in a piece of music. An "Entrainment Parameter" (EP) and/or EP ratio parameter can provide a measure of how closely the user's step interval times are in phase with the music's beat interval times. A sequence of EP values can be suitable for indicating if the person is 'entraining' with the music and can be evaluated, for example, using an average rolling window of time and filtering out natural fluctuations.

For a healthy walker, they have the ability to take equivalent length and interval steps on both sides of their body with consistent variability. However, this becomes more complicated for a walker with an unhealthy gait. A person that has an aberrant gait (e.g. from stroke, MS, PD, osteoarthritis, etc.) can actually have a difficult time entraining on both feet. This is because, for example, the patient lacks the control and/or the confidence on one of the sides of their body. Thus, testing results can reveal good entrainment on the patient's more controlled step side, while revealing relatively poorer entrainment (e.g., a high variability in step times or step onset times on the other foot) for the less controlled step side.

This side-to-side variability phenomenon is not limited to gait, and can occur and can apply to other repetitive motion activities such as upper or lower extremity motions. Accordingly, while exemplary embodiments are described in the context of systems and methods for gait-training, the systems and methods can similarly be implemented to treat other repetitive motion activities.

As described above in relation to Step 1822, a symmetry analysis can be applied to the sensor data collected from respective feet or other body locations and a determination can be made regarding the symmetry of the patient's gait or other repetitive motions. Moreover, in accordance with one or more embodiments, the systems and methods disclosed herein are specifically configured to identify, account for and overcome (i.e., reduce) the variability of entrainment results between the sides of the body, including both upper and lower extremities. This is achieved by the system evaluating and training the sides of the body differentially.

To overcome the variability caused by one foot, according to a salient aspect, the system can be configured to select only one of the patient's feet to be used in the entrainment calculation. That selected side is referred to as the "entrainment side." The selection of a side to focus the entrainment calculation can be beneficial in some circumstances, because entrainment measurements from monitoring both sides can be less useful for some patients that have unhealthy gaits. In the exemplary embodiments described herein, the relatively better side of the patient can be selected as the entrainment side. However, it should be understood that an underperforming side (e.g., the more affected side of the patient's body), can be selected as the entrainment side, as this approach can be more beneficial for some afflictions and related therapies. The process implemented by the system for selecting a particular foot over another could involve various strategies or considerations, including, for instance: which side of the patient's body achieves the most consistent steps; the side that has the least amount of variability in steps (e.g. as determined from a standard deviation and/or mean value of gait related parameters); the side that entrains the best in a head-to-head comparison between sides, among others. The process for selecting a foot could also be a combination of the above options. In addition or alternatively, an adaptive or self-learning strategy could be applied. Any of these strategies could be used by the system while a person is walking with sensors on and with or without the assistance of rhythmic cues.

In addition or alternatively to the foregoing approaches for selecting the entrainment side, the system can also be configured to evaluate the EP specific to a selected foot. In such an embodiment, the EP and related equations as shown and discussed previously, would be calculated by the system using the time difference between the repetitive motion of the selected side compared to the period between alternating rhythmic components or beats in the audio content (e.g., the auditory stimulus cues that correspond to the steps made by the selected foot). As can be appreciated, the rhythmic components (e.g., beats) of the auditory stimulus (e.g., music) can be arranged for the patient to step with a first foot in relation to a first beat and step with the other foot in relation to a subsequent beat. Accordingly, the timing of steps performed using the entrainment side are evaluated in view of the timing of alternating rhythmic components.

For example, in one embodiment, the system can be configured to perform a baseline calculation during a scenario where a person walks with sensors and no music. Based on the received biomechanical feedback data captured by the system from the sensors, a comparison calculation can be made to determine which side gets the closest to the actual number of steps taken. The system then selects that side as the "entrainment side." Similarly, during this same setup, a calculation could be made on the side that has the lowest coefficient of variance (CV), variability, or standard deviation. That side is then selected as the entrainment side. In another embodiment, the system can be configured to select an "entrainment side" while the patient uses a cane or other device. In this case, the entrainment side may be left, right, the side of the body on which a cane is held, or the side of the body reciprocal to the side holding the cane.

In addition or alternatively, the system is configured to collect biomechanical data while a person is walking and while listening to audio content, which could be either music or a metronome sound, for example. The system can be configured to calculate both a right foot and left foot EP and compare the respectively calculated EP to select the entrainment side. For instance, the side that has the best entrainment parameter (e.g. produces a result that is more consistently entrained) over a specific period of time can be selected and used for the remainder of the gait training session as the entrainment side.

In addition or alternatively, in some embodiments, the system can be configured to determine and compare the gait cycle time (GCT) variability for each foot. Various types of repetitive motion cycles are described herein, by way of background in the above discussion of window/gating techniques, for example. An analysis that calculates the lowest GCT variability (e.g. most stable intervals) could be used by the system to inform the entrainment side selection. This determination can be important since the side with the most consistent periodicity will more likely be the side that matches the beat intervals of the music. It should be further noted that this technique can also enable the system to effectively function when only a single sensor is used at a body location other than the feet such as a motion sensing wearable device or smartphone. In this case, the alternating pattern of lower variability values would indicate the entrainment side.

There are multiple phases of gait that fall into the two main categories: "swing" and "stance". Within those phases are further phases: heel strike, foot flat, mid-stance, heel off, toe-off, mid swing and end swing. When gait phases are evaluated from an IMU or sensor, and someone has an impaired gait, there is often error in some of the phases from step to step. Even though there is error there can be one or more parts of the gait that are more consistent. In addition to picking the entrainment side, according to a further salient aspect, the system can be configured to select a particular gait phase of motion to be used for step, step onset detection and the related entrainment calculation as mentioned in the above gait-training examples. This expands on the method introduced above as it relates to detecting the onset timestamp of a step (the "gate analysis"). In some embodiments, the gait phase of motion that is selected can often be one that has the most consistency and/or the highest amplitude. Consistency of the gait feature being evaluated for entrainment or step onset time detection purposes can be important to reliably determine whether the patient is walking entrained to the beat (e.g. if an inconsistent gait phase is selected, a patient could potentially be walking on beat, but the gait fluctuation can skew the system's data-based calculation providing false-negative results). As mentioned above, there are multiple phases of the gait cycle, which could include the heel strike, mid-stance, toe-off and many different segments of phases between these points. This can all be part of the gait cycle and the time for full completion of the gait cycle can be referred to as the gait cycle time.

When deciding the timing of the step to use as part of the EP entrainment calculation, a strategy is preferably used by the system to pick a portion of the gait cycle. This becomes particularly more relevant as a motion, like gait, is degraded in quality. In this instance, the system can be configured to implement a method to ensure robustness in a degraded gait that can include measuring which detected gait phase presents the strongest (e.g. most frequently occurring) by a voting system. One example of a voting system would be tallying each reported gait phase over a period of 1 minute. In an ideal gait, each gait phase tally would be the same, e.g. there would be equal numbers reported for each phase detected by the system. In a compromised gait, typical of a patient in rehab, the number of each reported gait phases is affected by the patient's biomechanical pattern of movement, such as spatial circumduction. In this case, the gait phase that is reported with the highest frequency would correlate to the gait phase with the highest reliability. The voting system would select this highest ranked phase as demarking the step time (e.g. the gait phase "gate analysis" boundary) for the purpose of calculating the entrainment precision. In the case of a tie, other parameters can be used to select the phase such as variability, precision, or accuracy. In some embodiments, the system can be configured to review the variability or other parameters first followed by the counting method. In some embodiments, an entrainment precision could be calculated using each phase, selecting the one with the strongest entrainment precision as the preferred phase.

In addition or alternatively, the system can implement a method that includes monitoring the incoming gait phases and using an algorithmic approach to "hop" to a different gait phase in the event that it presents more reliably at a later stage. This scenario may occur as a patient increases or decreases their velocity, or other material changes about their gait happen. Many such "signal strength" strategies are used in RF communications, and the system can implement similar concepts here to help pull out the best biomechanical signal for patients whose gait patterns are compromised by disease or injury.

In some scenarios, a user may place the sensors on the wrong feet, for example, mounting the left sensor on the right foot. This could cause errors in calculating symmetry and entrainment. Accordingly, the system can be configured to implement a method that compares spatial movement patterns to determine if the sensors are placed on the wrong foot and thus prompt the system to "auto-correct." More specifically, after detecting this error state, the system can be configured to swap data inputs from each foot by software so as not to adversely affect the therapy or offline processing of gait data.

In addition or alternatively, in some embodiments, the identification of the side of the user that is the "affected" side (e.g., after a stroke) could be provided as an input to the system. The affected side often has a physical deficiency, such as a hemipelagic or gait circumduction pattern that impedes a user's step timing on that side. The system can be configured to use any such inputs to confirm any empirically derived determination, including or in combination with the methods discussed above.

Upon selection of the entrainment side and then the particular parameter(s) (e.g., gait phase) being monitored for purposes of calculating the EP, the system can be configured to provide side-specific repetitive motion therapy utilizing the exemplary systems and methods described above. For example, the gait-training systems and techniques described in connection with FIG. 18 can be adapted to provide side-specific repetitive motion therapy. More specifically, based on the biomechanical sensor data monitored from the selected entrainment side, the EP for a patient can be evaluated and EP can be utilized to dynamically generate rhythmic auditory stimulus cues for the patient as described, for example, in connection with FIG. 18. Moreover, although EP can be calculated based on the biomechanical data captured from the selected entrainment side in this exemplary implementation and is thus described as being "side-specific," it should be understood that the rhythmic auditory stimulus cues can be output to assist with entrainment of both sides of the patient's body.

Figure 32:
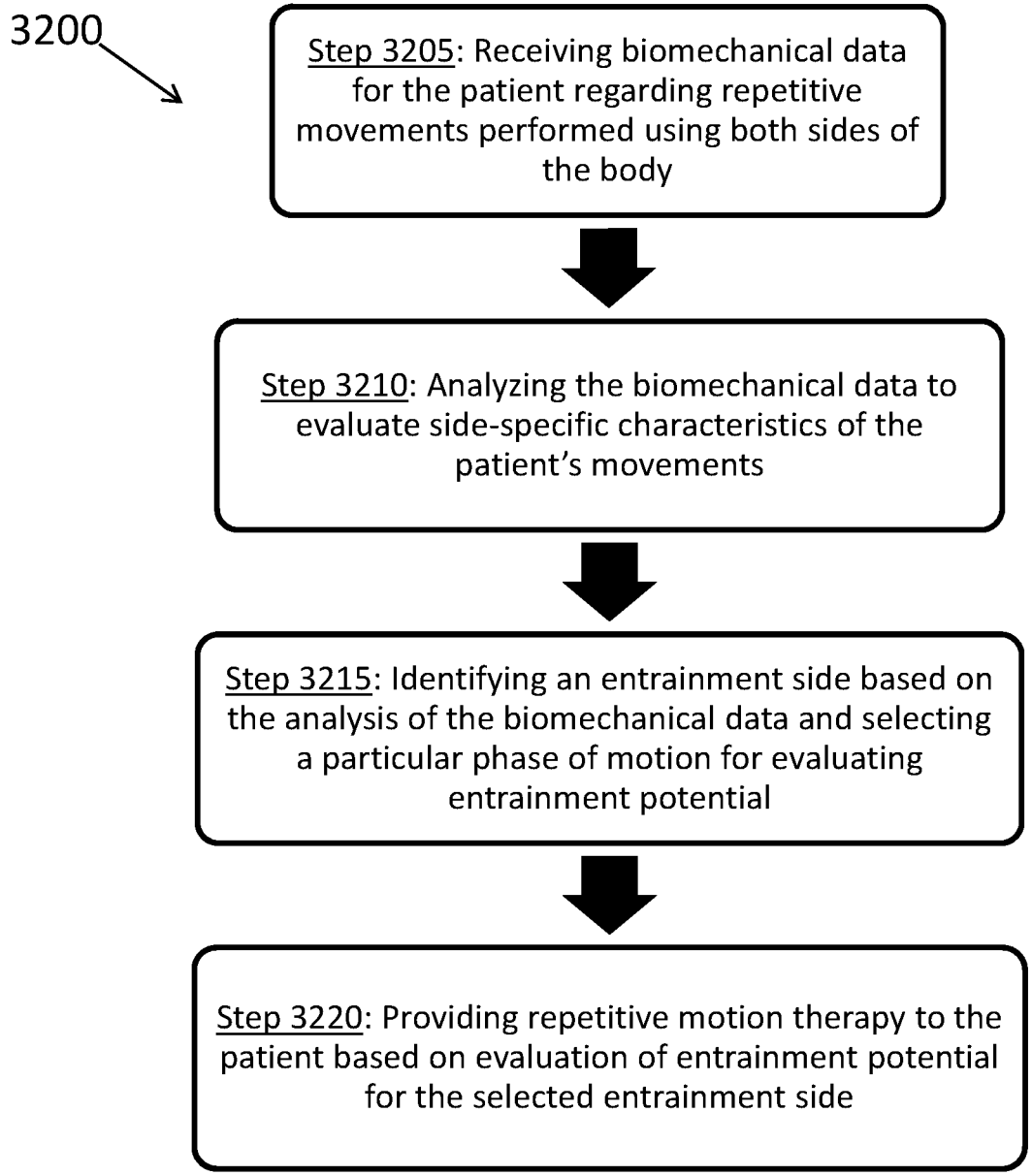
FIG. 32 illustrates an implementation of a technique for side-specific repetitive motion training of a patient in accordance with exemplary embodiments of the disclosed subject matter.

In view of the foregoing it can be appreciated that what is disclosed is a method for rehabilitation of a patient having a physical impairment by providing music therapy. The method being implemented on a computer system having one or more physical processors configured by machine-readable instructions which, when executed perform the method. In one or more embodiments, as shown in FIG. 32, the method 3200 includes the step of receiving 3205 biomechanical data for the patient regarding repetitive movements of the patient performed using both sides of the body. The method also includes analyzing 3210 the biomechanical data to evaluate side-specific characteristics of the patient's movements, for instance, the symmetry of the patient's motion or to otherwise determine the entrainment potential of each side of the patient's body performing the repetitive motion activity, respectively. The method also includes identifying 3215 an entrainment side based on the analysis of the biomechanical data. The entrainment side is a particular side of the body that is analyzed to define the therapy that can be delivered to the patient to train the entrainment side, the opposite side, or both sides. It is important to note that after the analysis of selecting an entrainment side is complete, it is possible that there is no need to deem a single side as the entrainment side due to adequate temporal symmetry in their physical movement. In these cases, onset times from both left and right sides can be used for calculating the EP. In addition to picking the entrainment side at step 3215, according to a further aspect, the method includes selecting a particular phase of motion which is monitored and used to measure the entrainment potential of the patient. After selection of the entrainment side and the particular phase of motion being monitored for purposes of calculating EP, the method includes the step of providing side-specific repetitive motion therapy 3225 to the patient. For instance, the method includes evaluating the entrainment potential specific to the selected side of the body, e.g., while providing side-specific repetitive motion therapy. More specifically, entrainment potential can be calculated based on the time difference between the repetitive motion of the selected side compared to the period between alternating rhythmic components or beats in the audio content.

According to a further aspect, the step for providing repetitive motion therapy to the patient using a single side, namely the selected entrainment side, to calculate EP includes the steps of: receiving biomechanical data from the patient regarding repetitive movements of at least the selected entrainment side of the patient and determining a baseline condition for the patient's entrainment side; and determining a baseline beat tempo having a constant frequency based on the baseline condition. The step of providing therapy also includes: providing music (or more generally auditory stimulus) to the patient wherein the music has beat signals (or more generally a rhythmic component) that are output at respective beat times. Outputting the music can also include providing a cue to the patient to perform each repetitive movement in time with an associated baseline beat signal. It should be understood that the cue need not be a specific prompt provided in addition to the music. The cue can be the beats of the music that serve to consciously or subconsciously cue the patient to perform the movements in time with the beats. Additionally, the rhythmic cue can be provided for each repetitive movement performed using either side of the patient's body.

The step of providing therapy further includes the step of receiving time-stamped biomechanical data of the patient relating to the repetitive movements performed by the patient using at least the entrainment side in time with the beat signals. Biomechanical data can be received for the patient regarding repetitive movements performed using either side of the patient's body. The step of providing therapy further includes the step of: analyzing the time-stamped biomechanical data to identify an onset time for the particular phase of motion for one of more cycles of the repetitive movement performed using the entrainment side. Additionally, the method includes calculating the entrainment potential based on the onset time and respective output times of the associated beat signal. More specifically, calculating the entrainment potential can comprise determining a delay between the onset time of the particular phase of motion for each repetitive movement and the respective output time of the associated beat signal. The step of providing therapy further includes the step of modifying the auditory stimulus as a function of the calculated entrainment potential. For instance, modifying the auditory stimulus can include modifying a baseline beat tempo based on the calculated entrainment potential and determining whether a goal beat tempo has been reached. While exemplary embodiments of the systems and methods for providing side-specific repetitive motion therapy have discussed in relation to gait training, it should be understood that the systems and methods are similarly applicable to training other portions of the body.

The above systems, devices, methods, processes, and the like may be realized in hardware, software, or any combination of these suitable for an application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in several ways. At the same time, processing may be distributed across devices such as the various systems described above, or all the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless an order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure.

What is claimed is:

1. A method for rehabilitation of a patient having a physical impairment by providing repetitive motion therapy in which the patient is provided auditory stimulus having beat signals and the patient attempts to perform repetitive movements using a first side and an opposite second side of the patient's body in time with the beat signals, the method being implemented on a computer system having a processor configured by machine-readable instructions which, when executed perform the method, the method comprising:
   receiving, at the computer system, biomechanical data for the patient regarding repetitive movements of the patient performed using the first and second sides of the body respectively;
   selecting, by the computer system based on the biomechanical data, an entrainment side, wherein the entrainment side is one of the first or the second side of the body;

performing, by the computer system, repetitive motion therapy by:
- outputting, to the patient, auditory stimulus comprising beat signals output at respective beat times,
- receiving time-stamped biomechanical data of the patient relating to the repetitive movements performed by the patient using at least the entrainment side in relation to the beat signals,
- calculating an entrainment potential for the entrainment side, wherein the entrainment potential is calculated by comparing a timing of the repetitive movements performed by the patient using the entrainment side to the respective beat times of the beat signals; and
- modifying the auditory stimulus as a function of the calculated entrainment potential.

2. The method of claim 1, wherein each repetitive movement is a cyclical motion comprising a plurality of phases, and the method further comprising:
selecting, with the computer system, a particular phase among the phases of the repetitive movement, and wherein the entrainment potential is calculated based on a timing of the particular phase for each cycle of the repetitive movement performed by the patient using the entrainment side.

3. The method of claim 2, wherein the step for providing repetitive motion therapy further comprises:
analyzing the time-stamped biomechanical data to identify a respective onset time of the particular phase for each of multiple cycles of the repetitive movement performed using the entrainment side; and
calculating the entrainment potential based on the respective onset times and respective beat times of corresponding beat signals among the beat signals.

4. The method of claim 3, wherein the entrainment potential is calculated by comparing a period between the respective onset times of the particular phase for each of multiple cycles to a period between alternating beats in the beat signal.

5. The method of claim 3, wherein calculating the entrainment potential comprises measuring a delay between the respective onset time of the particular phase for each of multiple cycles and the respective beat times of corresponding beat signals among the beat signals.

6. The method of claim 1, wherein selecting the entrainment side comprises:
determining, based on the biomechanical data, a symmetry of the repetitive movements performed using the first side relative to the repetitive movements performed using the second side of the body, and wherein the entrainment side is selected based on the determined symmetry.

7. The method of claim 1, wherein the step of selecting the entrainment side comprises:
measuring, from the biomechanical data, one or more of:
- a consistency of the repetitive movement respectively for each side of the body,
- a variability in the repetitive movement respectively for each side of the body,
- an entrainment potential respectively for each side of the body; and selecting the entrainment side as a function of the result of the measuring step.

8. The method of claim 7, wherein the step of selecting the entrainment side comprises measuring, from the biomechanical data, the variability and wherein the variability measured is a gait cycle time (GCT) variability measured respectively for each side of the body.

9. The method of claim 1, wherein the step of modifying the auditory stimulus includes adjusting a timing of the beat signals based on the calculated entrainment potential.

10. The method of claim 1, further comprising, prior to the step of performing repetitive motion therapy:
determining, based on the biomechanical data, a baseline condition for the patient's entrainment side; and
defining a baseline beat tempo for the auditory stimulus as a function of the baseline condition, wherein the baseline beat tempo has a constant frequency.

11. A system for rehabilitation of a patient having a physical impairment by providing repetitive motion therapy in which the patient is provided auditory stimulus having beat signals and the patient attempts to perform repetitive movements using a first side and an opposite second side of the patient's body in time with the beat signals, the system comprising:
a computer system having a processor configured by machine-readable instructions to:
- receive biomechanical data for the patient regarding repetitive movements of the patient performed using the first and second sides of the body respectively, wherein the biomechanical data is measured using a sensor associated with the patient;
- select, based on the biomechanical data, an entrainment side, wherein the entrainment side is one of the first or the second side of the body;
- perform, by the processor, repetitive motion therapy by:
  - outputting to the patient auditory stimulus comprising beat signals output at a respective beat times,
  - receiving time-stamped biomechanical data of the patient relating to the repetitive movements performed by the patient using at least the entrainment side in relation to the beat signals, wherein the time-stamped biomechanical data is measured using a sensor associated with the patient;
  - calculating an entrainment potential for the entrainment side, wherein the entrainment potential is calculated by comparing a timing of the repetitive movements performed by the patient using the entrainment side to the respective beat times of the beat signals; and
  - modifying the auditory stimulus as a function of the calculated entrainment potential.

12. The system of claim 11, further comprising:
an auditory output device for providing the auditory stimulus to the patient; and
the sensor associated with the patient and measuring the time-stamped biomechanical data.

13. The system of claim 11, wherein the repetitive movement is a cyclical motion comprising a plurality of phases, and wherein the processor is further configured to select a particular phase among the phases of the repetitive movement, and wherein the entrainment potential is calculated based on a timing of the particular phase for each cycle of the repetitive movement performed by the patient using the entrainment side.

14. The system of claim 13, wherein the processor is configured to provide repetitive motion therapy by:
analyzing the time-stamped biomechanical data to identify a respective onset time of the particular phase for each of multiple cycles of the repetitive movement performed using the entrainment side; and
calculating the entrainment potential based on the respective onset times and respective beat times of corresponding beat signals among the beat signals.

15. The system of claim 11, wherein the processor is configured to select the entrainment side by determining, based on the biomechanical data, a symmetry of the repetitive movements performed using the first side relative to the repetitive movements performed using the second side of the body, and wherein the entrainment side is selected based on the determined symmetry.

16. The system of claim 11, wherein the processor is configured to select the entrainment side by measuring, from the biomechanical data, one or more of:
   a consistency of the repetitive movement respectively for each side of the body,
   a variability in the repetitive movement respectively for each side of the body, and
   an entrainment potential respectively for each side of the body; and
   wherein the entrainment side is selected as a function of the result of the measuring step.

17. The system of claim 11, wherein the processor is configured to modify the auditory stimulus by adjusting a timing of the beat signals based on the calculated entrainment potential and based on a goal beat tempo.

18. The system of claim 11, wherein the processor is configured to, prior to the step of performing repetitive motion therapy:
   determine, based on the biomechanical data, a baseline condition for the patient's entrainment side; and
   define a baseline beat tempo for the auditory stimulus as a function of the baseline condition, wherein the baseline beat tempo has a constant frequency.

\* \* \* \* \*